United States Patent
Toda et al.

(10) Patent No.: US 11,713,988 B2
(45) Date of Patent: Aug. 1, 2023

(54) FLOW RATE-VELOCITY CALCULATOR, FLOW RATE-VELOCITY SENSOR DEVICE, FLOW RATE DEVICE, AND FLOW RATE-VELOCITY CALCULATION METHOD

(71) Applicant: KYOCERA Corporation, Kyoto (JP)

(72) Inventors: Keisuke Toda, Kirishima (JP); Shougo Matsunaga, Kirishima (JP); Yushi Nagasaka, Ritto (JP)

(73) Assignee: KYOCERA Corporation, Kyoto (JP)

( * ) Notice: Subject to any disclaimer, the term of this patent is extended or adjusted under 35 U.S.C. 154(b) by 386 days.

(21) Appl. No.: 17/042,504

(22) PCT Filed: Mar. 28, 2019

(86) PCT No.: PCT/JP2019/013727
§ 371 (c)(1),
(2) Date: Sep. 28, 2020

(87) PCT Pub. No.: WO2019/189630
PCT Pub. Date: Oct. 3, 2019

(65) Prior Publication Data
US 2021/0025742 A1    Jan. 28, 2021

(30) Foreign Application Priority Data
Mar. 28, 2018 (JP) .................. 2018-062562

(51) Int. Cl.
*G01F 1/661*    (2022.01)
*A61B 5/026*    (2006.01)

(52) U.S. Cl.
CPC ............ *G01F 1/661* (2013.01); *A61B 5/0261* (2013.01)

(58) Field of Classification Search
CPC ............................. G01F 1/661; A61B 5/0261
(Continued)

(56) References Cited

U.S. PATENT DOCUMENTS 5,526,109 A * 6/1996 Johnson .................. G01P 3/366
                                                             356/28.5
6,454,722 B1 * 9/2002 Numajiri .............. A61B 3/1241
                                                             600/399
(Continued)

FOREIGN PATENT DOCUMENTS

EP    2837327 A1    2/2015
EP    3045876 A1    7/2016
(Continued)

OTHER PUBLICATIONS

Translation of WO-2009139029-A1 (Year: 2009).*
(Continued)

*Primary Examiner* — Nathaniel T Woodward
(74) *Attorney, Agent, or Firm* — Volpe Koenig

(57) ABSTRACT

A flow rate-velocity sensor device includes a package including a light receiver and a light emitter, a transparent substrate including a light shield, and a flow rate-velocity calculator. The flow rate-velocity calculator includes a receiver, a correction unit, an arithmetic unit, and a transmitter. The receiver receives data on a first power spectrum. The correction unit corrects the data received by the receiver to calculate a second power spectrum. The arithmetic unit calculates at least one of a flow rate or a flow velocity from the second power spectrum calculated by the correction unit. The transmitter transmits, to an external unit, at least one of the flow rate or the flow velocity calculated by the arithmetic unit.

18 Claims, 19 Drawing Sheets

(58) Field of Classification Search
USPC .......................................................... 356/28
See application file for complete search history.

(56) References Cited

U.S. PATENT DOCUMENTS

2008/0208011 A1    8/2008  Shuler
2011/0260176 A1   10/2011  Onoe et al.

FOREIGN PATENT DOCUMENTS

| JP | 07-092184 A | 4/1995 | |
| JP | 2010-520773 A | 6/2010 | |
| JP | 2018-007894 A | 1/2018 | |
| JP | 2018007894 A * | 1/2018 | ............. A61B 5/024 |
| WO | 2009/139029 A1 | 11/2009 | |
| WO | WO-2009139029 A1 * | 11/2009 | ........... A61B 5/0261 |
| WO | 2013/153664 A1 | 10/2013 | |
| WO | WO-2013153664 A1 * | 10/2013 | ........... A61B 5/0261 |
| WO | 2015/033469 A1 | 3/2015 | |

OTHER PUBLICATIONS

Translation of WO-2013153664-A1 (Year: 2013).*
Translation of JP-2018007894-A (Year: 2018).*
Schlindwein F S et al: "Real-Time Digital Processing of Doppler Ultrasound Signals and Calculation of Flow Parameters", Medical Progress Through Technology, Springer Verlag. Berlin, DE, vol. 20, No. 1/02, Jan. 1, 1994 (Jan. 1, 1994), pp. 81-89, XP000459487, ISSN: 0047-6552 pp. 84, 85.

* cited by examiner

FLOW RATE-VELOCITY CALCULATOR, FLOW RATE-VELOCITY SENSOR DEVICE, FLOW RATE DEVICE, AND FLOW RATE-VELOCITY CALCULATION METHOD

FIELD

The present invention relates to a flow rate-velocity calculator, a flow rate-velocity sensor device, a flow rate device, and a flow rate-velocity calculation method.

BACKGROUND

Flow rate-velocity sensor devices such as measurement sensors that easily and speedily measure biometric information including blood flow have been awaited. Measurement of blood flow uses, for example, the Doppler effect of light. When blood is illuminated with light, the light is scattered by blood cells, such as red blood cells. The frequency of the illuminating light and the frequency of the scattered light are used to calculate the traveling speed of the blood cells. A flow rate-velocity sensor device for measuring blood flow or other items described in, for example, Japanese Unexamined Patent Application Publication No. 7-92184 includes a substrate accommodating a light receiver and a light emitter, and a transparent substrate bonded to the upper surface of the substrate. The substrate partially covers the light emitter.

However, the flow rate-velocity sensor device described in Japanese Unexamined Patent Application Publication No. 7-92184 may not easily reflect the difference between high flow rates and low flow rates at a reference frequency, possibly causing inaccurate determination of the current flow rate.

BRIEF SUMMARY

A flow rate-velocity calculator according to an embodiment of the present invention includes a receiver, a correction unit, an arithmetic unit, and a transmitter. The receiver receives data on a first power spectrum. The correction unit corrects the data received by the receiver to calculate a second power spectrum. The arithmetic unit calculates at least one of a flow rate or a flow velocity from the second power spectrum calculated by the correction unit. The transmitter transmits data obtained through calculation by the arithmetic unit to an external unit.

A flow rate-velocity sensor device according to an embodiment of the present invention includes a package including a light receiver and a light emitter, a transparent substrate including a light shield, and a flow rate-velocity calculator.

A flow rate-velocity calculation method according to an embodiment of the present invention includes a first process of receiving a first power spectrum, a second process of correcting the first power spectrum received in the first process to calculate a second power spectrum, and a calculation process of calculating at least one of a flow rate or a flow velocity from the second power spectrum calculated in the second process.

DETAILED DESCRIPTION

Figure 1:
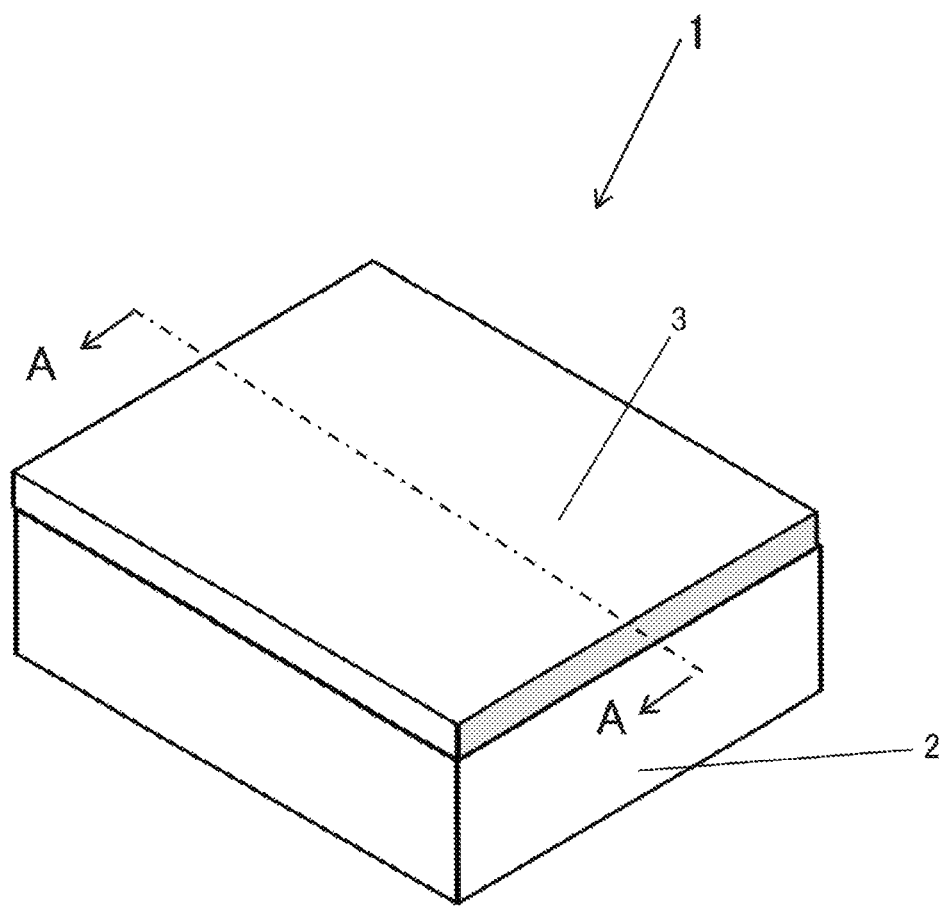
FIG. 1 is a perspective view of a flow rate-velocity sensor included in a flow rate-velocity sensor device according to an embodiment of the invention.
Figure 2:
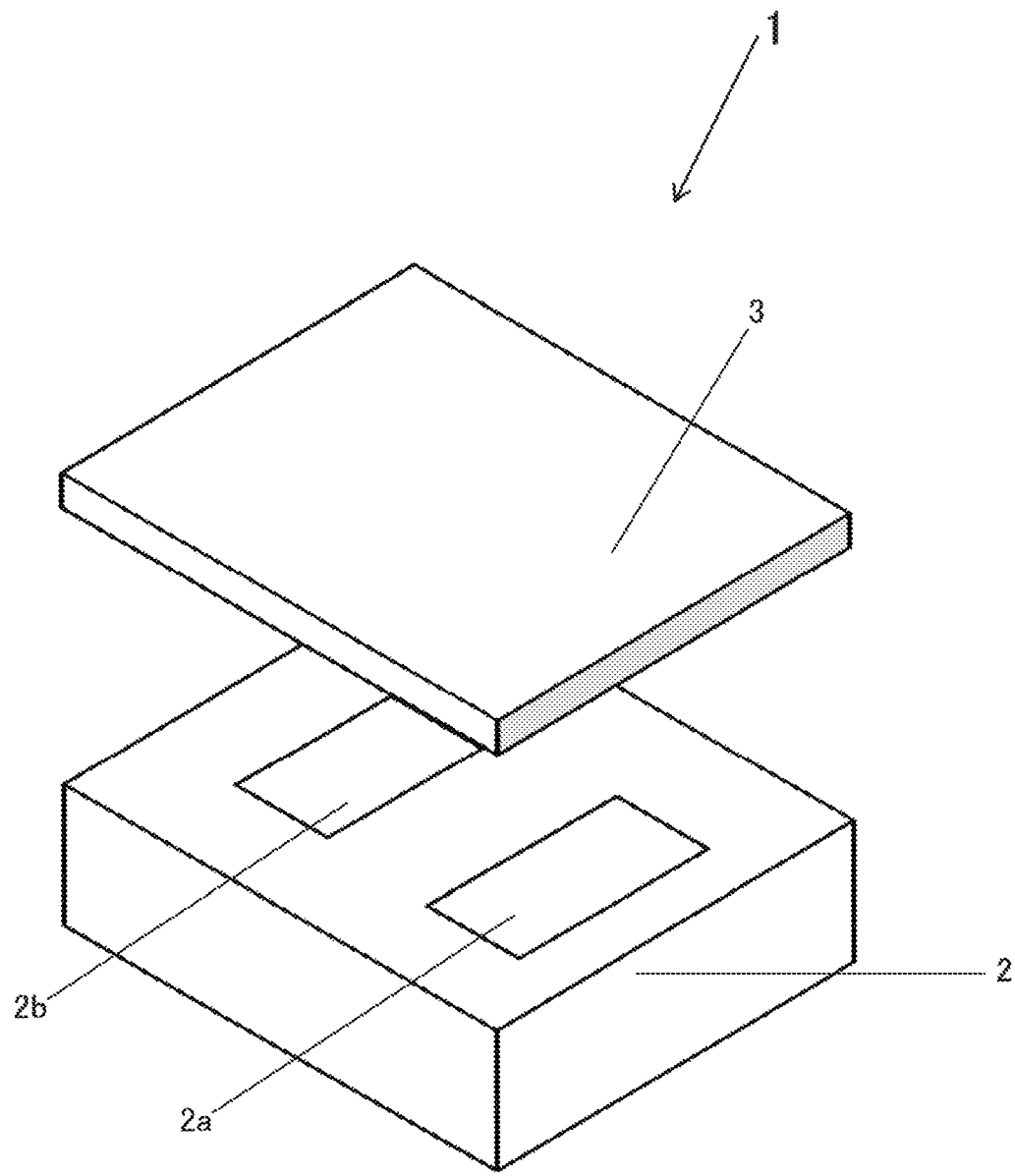
FIG. 2 is an exploded perspective view of the flow rate-velocity sensor included in the flow rate-velocity sensor device according to the embodiment of the invention.
Figure 3:
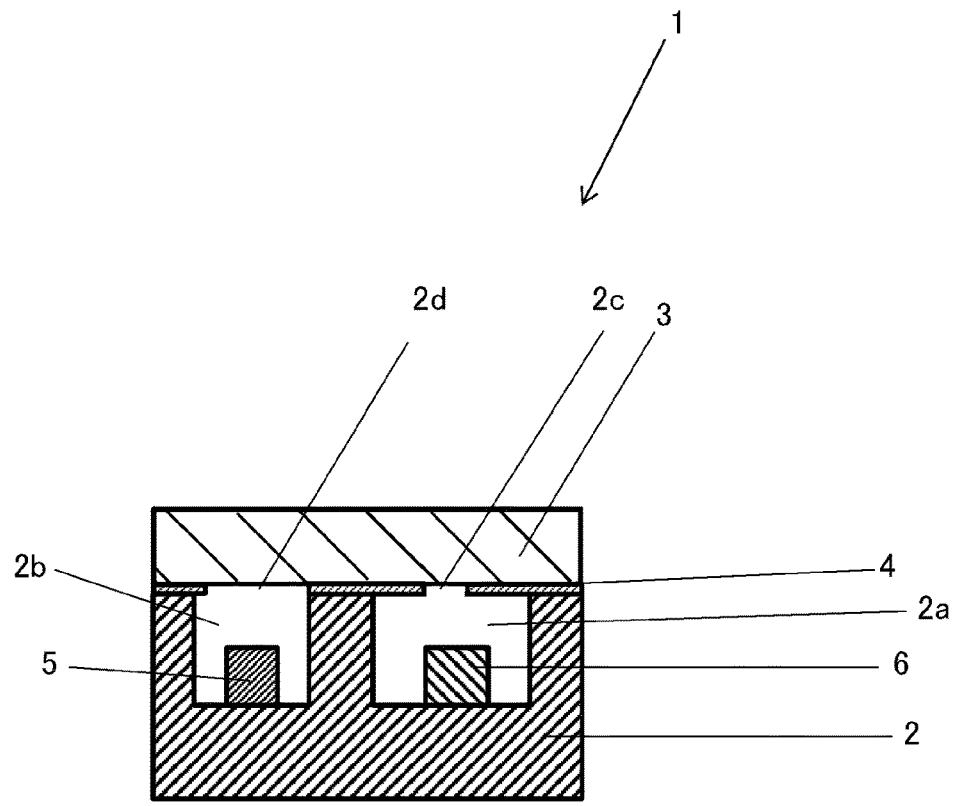
FIG. 3 is a cross-sectional view of the flow rate-velocity sensor included in the flow rate-velocity sensor device according to the embodiment of the invention, taken along line A-A of FIG. 1.
Figure 4:
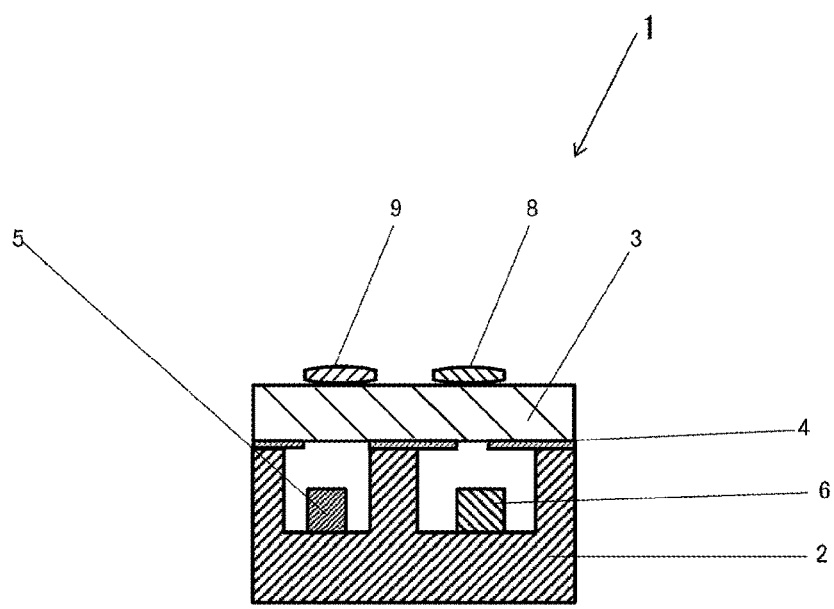
FIG. 4 is a cross-sectional view of a flow rate-velocity sensor included in a flow rate-velocity sensor device according to another embodiment of the invention.
Figure 5:
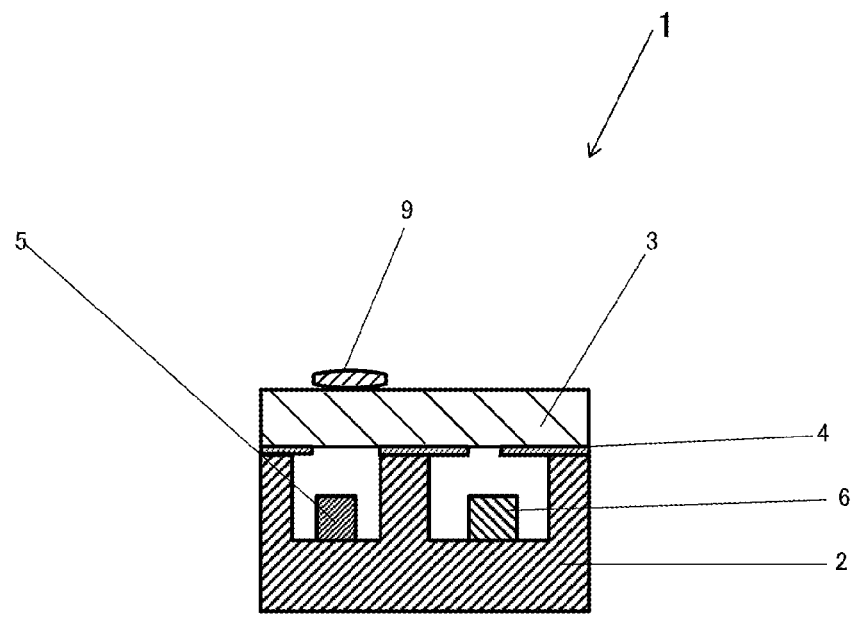
FIG. 5 is a cross-sectional view of a flow rate-velocity sensor included in a flow rate-velocity sensor device according to another embodiment of the invention.
Figure 6:
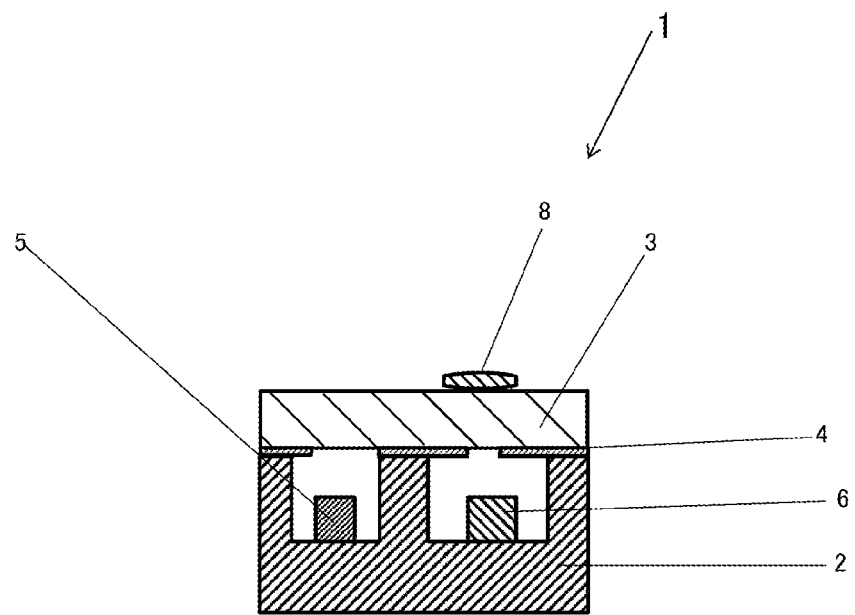
FIG. 6 is a cross-sectional view of a flow rate-velocity sensor included in a flow rate-velocity sensor device according to another embodiment of the invention.
Figure 7:
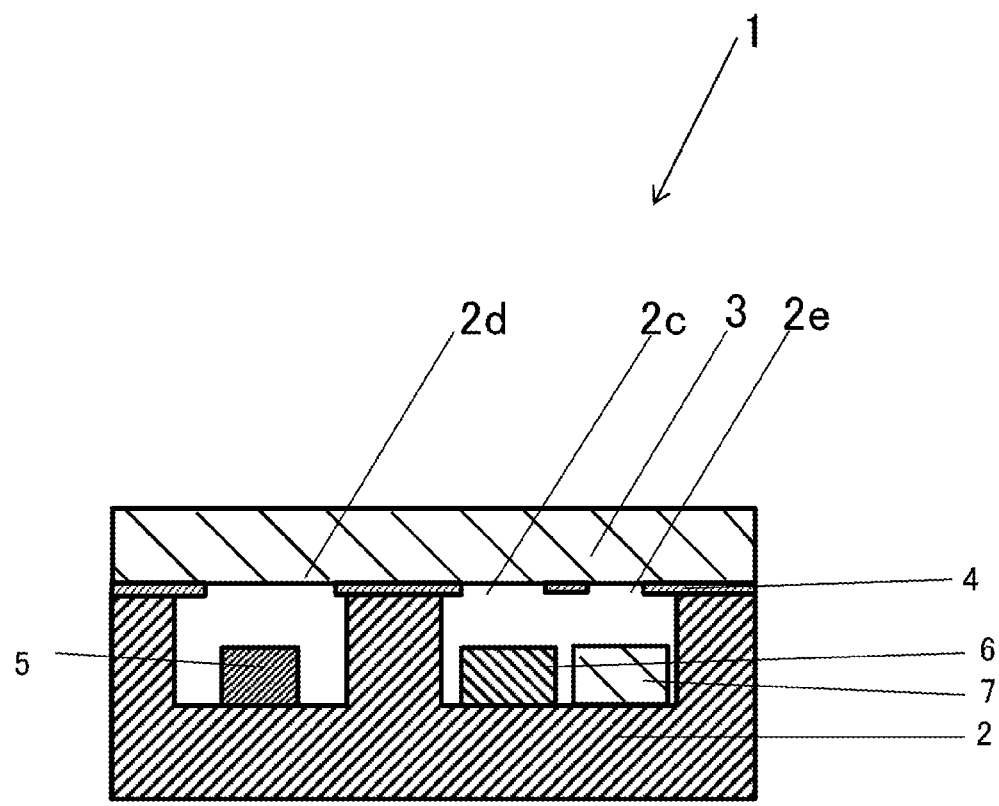
FIG. 7 is a cross-sectional view of a flow rate-velocity sensor included in a flow rate-velocity sensor device according to another embodiment of the invention.
Figure 8:
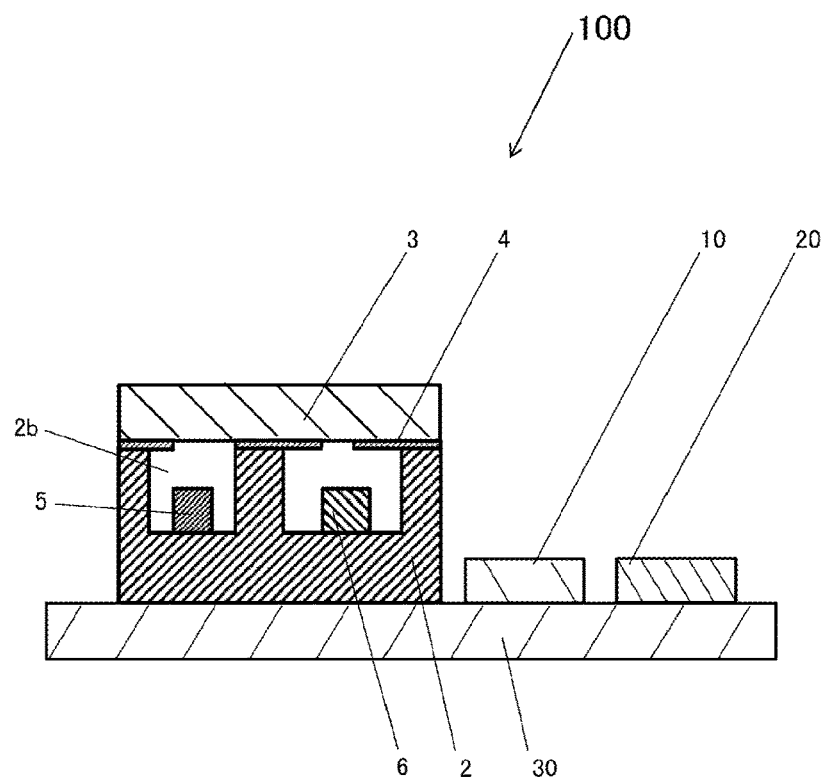
FIG. 8 is a cross-sectional view of a flow rate-velocity sensor device according to an embodiment of the invention.
Figure 9:
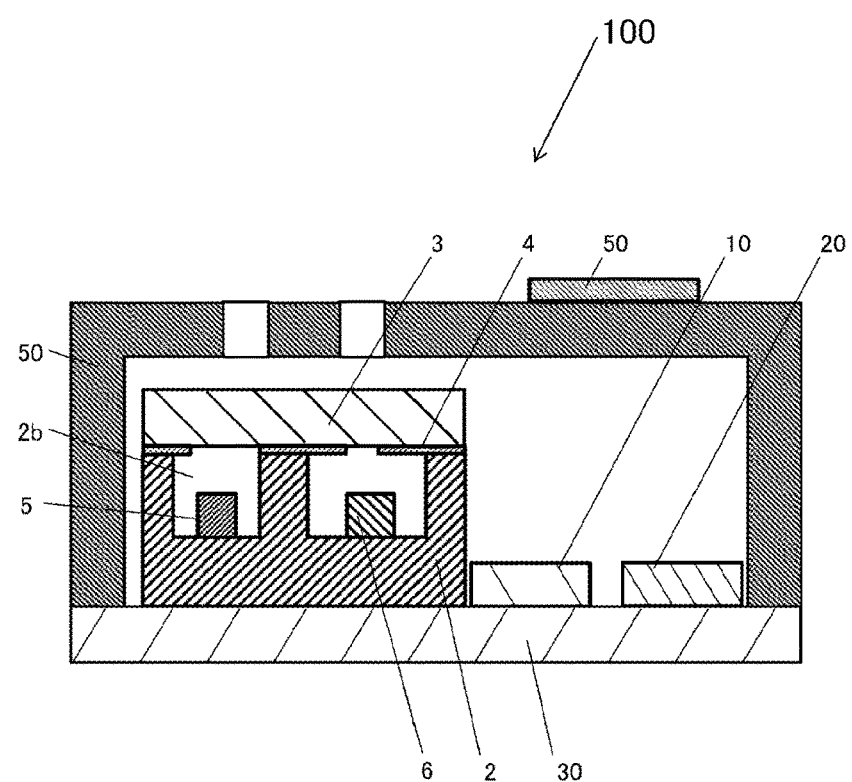
FIG. 9 is a cross-sectional view of a flow rate-velocity sensor device according to another embodiment of the invention.
Figure 10:
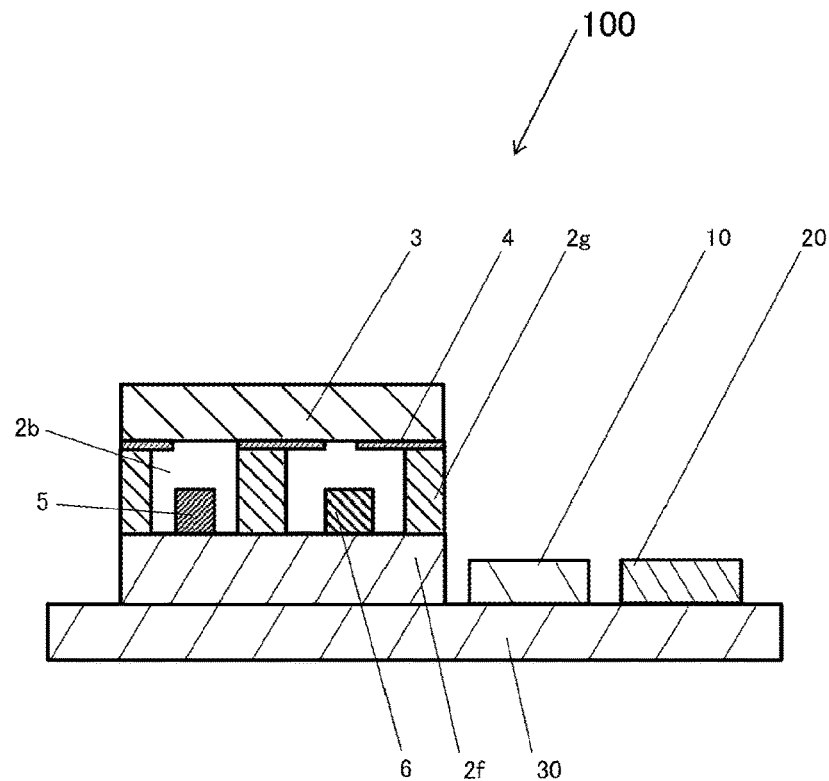
FIG. 10 is a cross-sectional view of a flow rate-velocity sensor device according to another embodiment of the invention.
Figure 11:
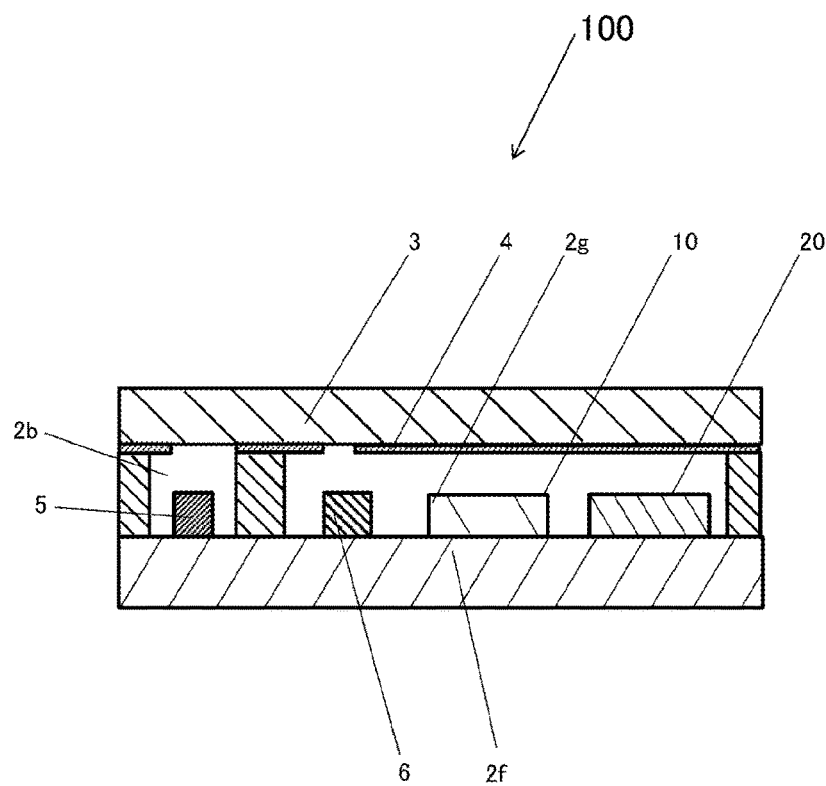
FIG. 11 is a cross-sectional view of a flow rate-velocity sensor device according to another embodiment of the invention.
Figure 12:
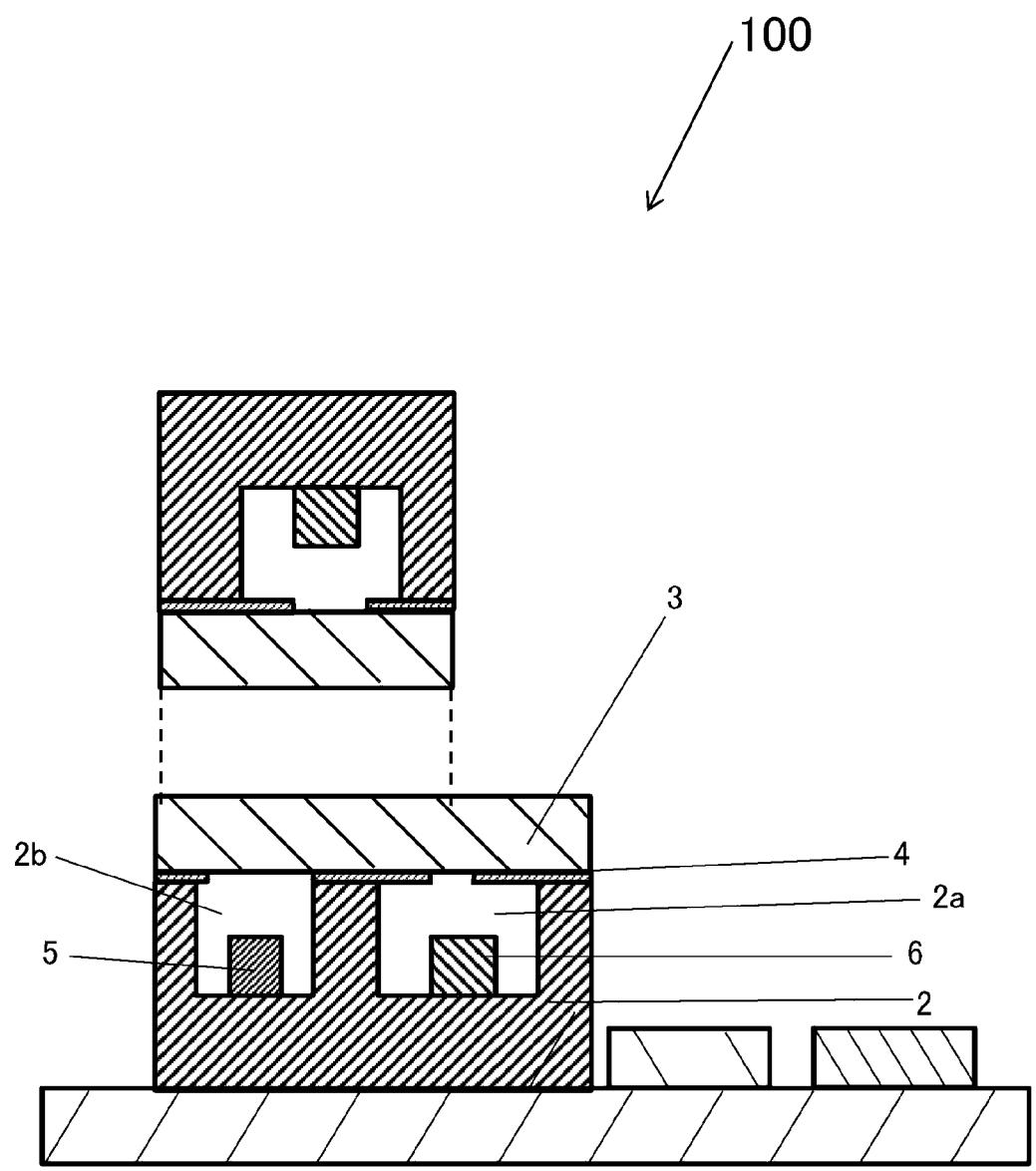
FIG. 12 is a cross-sectional view of a flow rate-velocity sensor device according to another embodiment of the invention.
Figure 13:
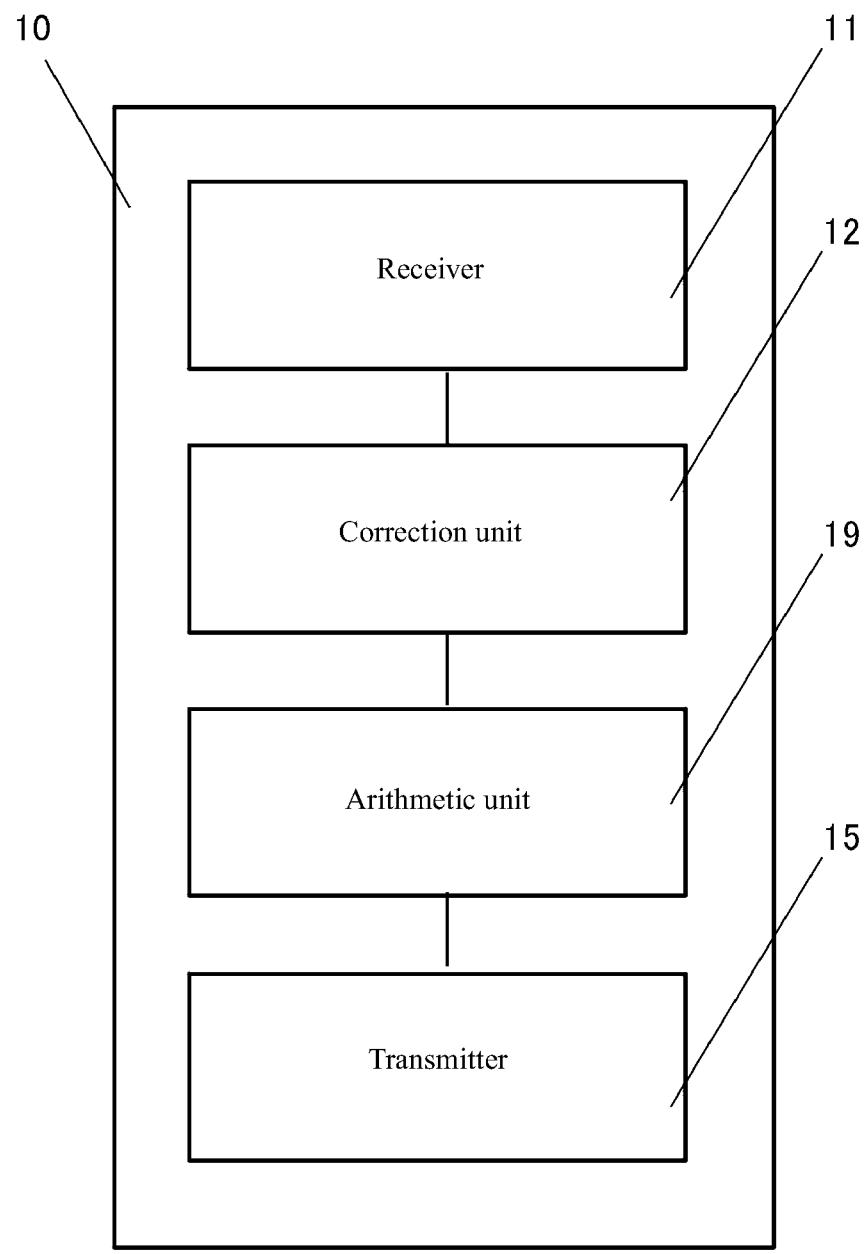
FIG. 13 is a block diagram of a flow rate-velocity calculator according to an embodiment of the invention.
Figure 14:
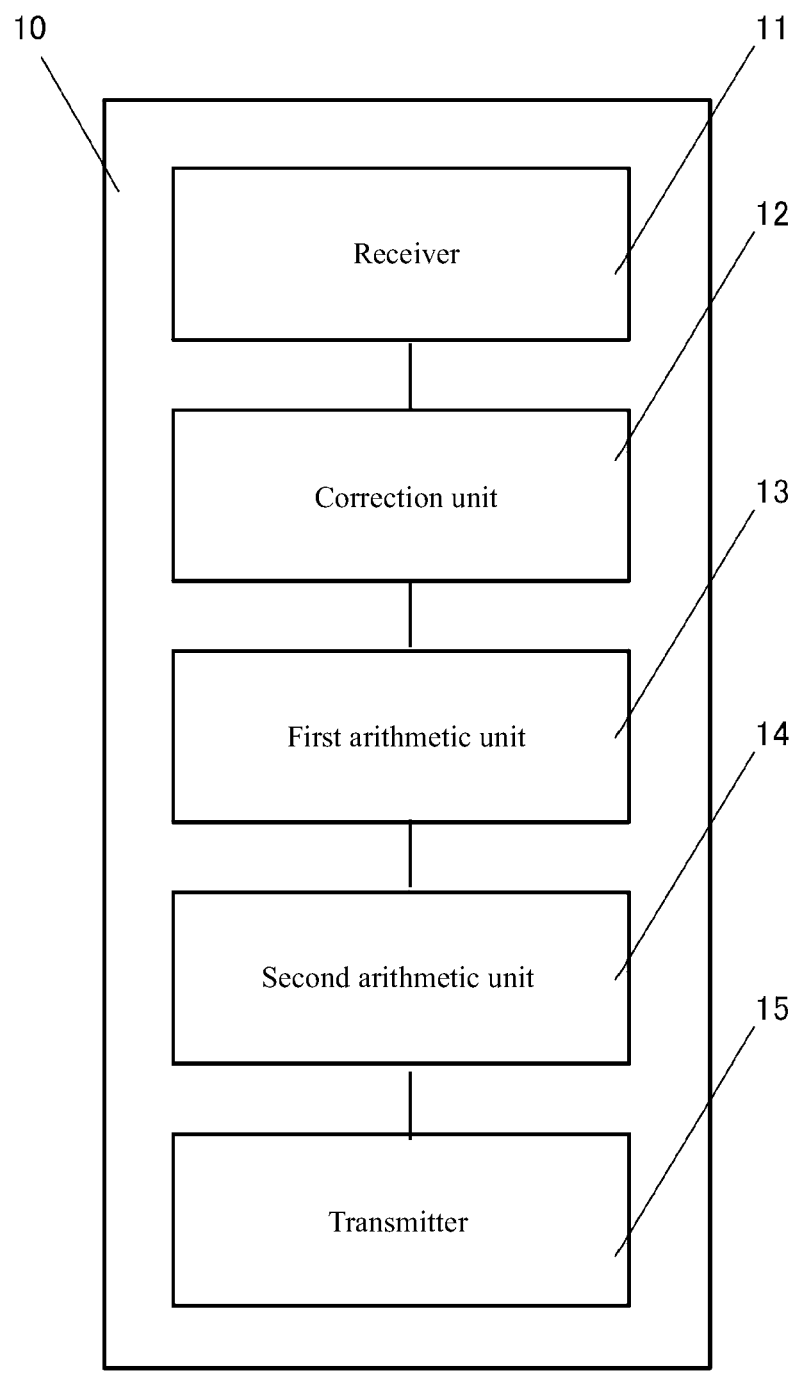
FIG. 14 is a block diagram of a flow rate-velocity calculator according to an embodiment of the invention.
Figure 15:
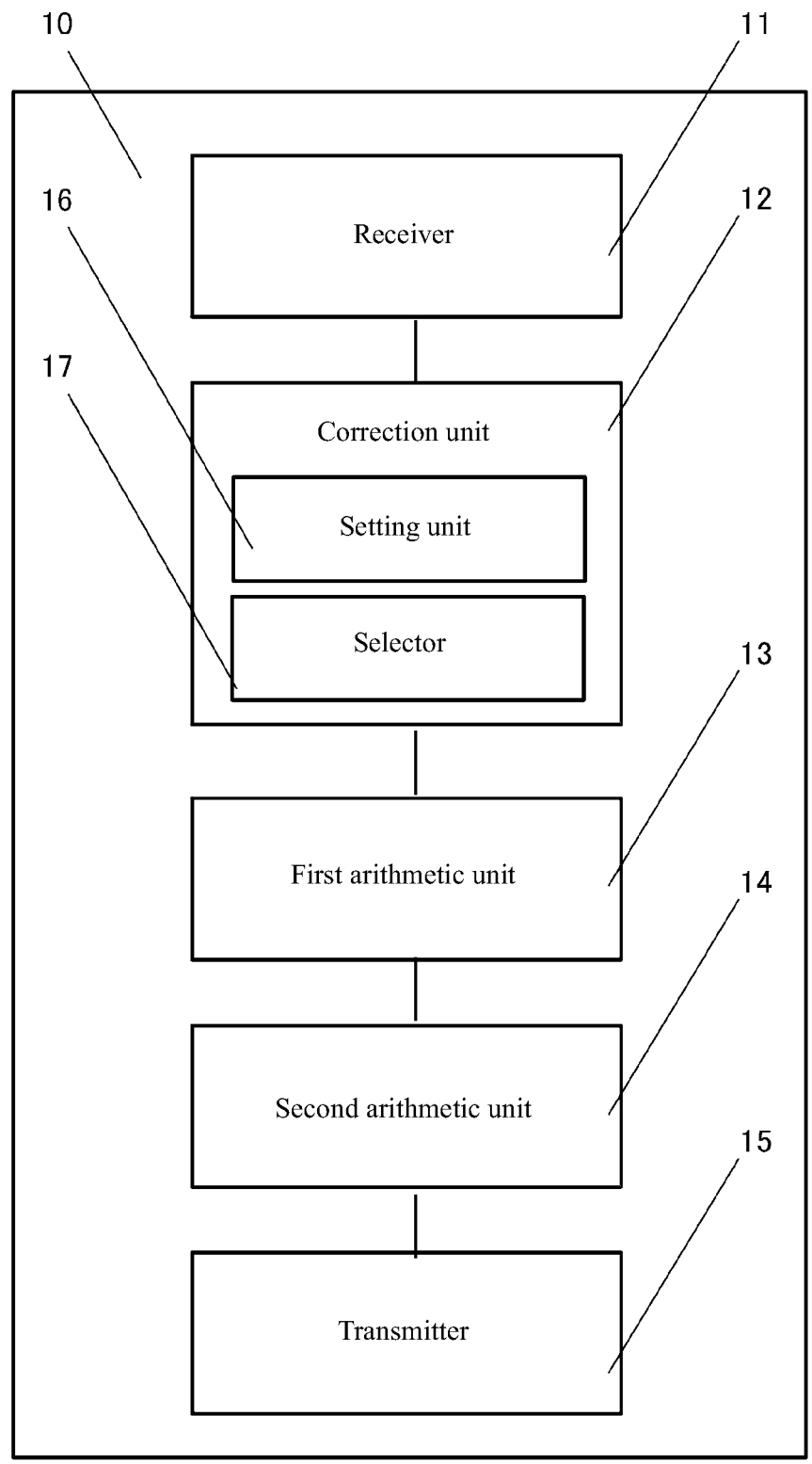
FIG. 15 is a block diagram of a flow rate-velocity calculator according to another embodiment of the invention.
Figure 16:
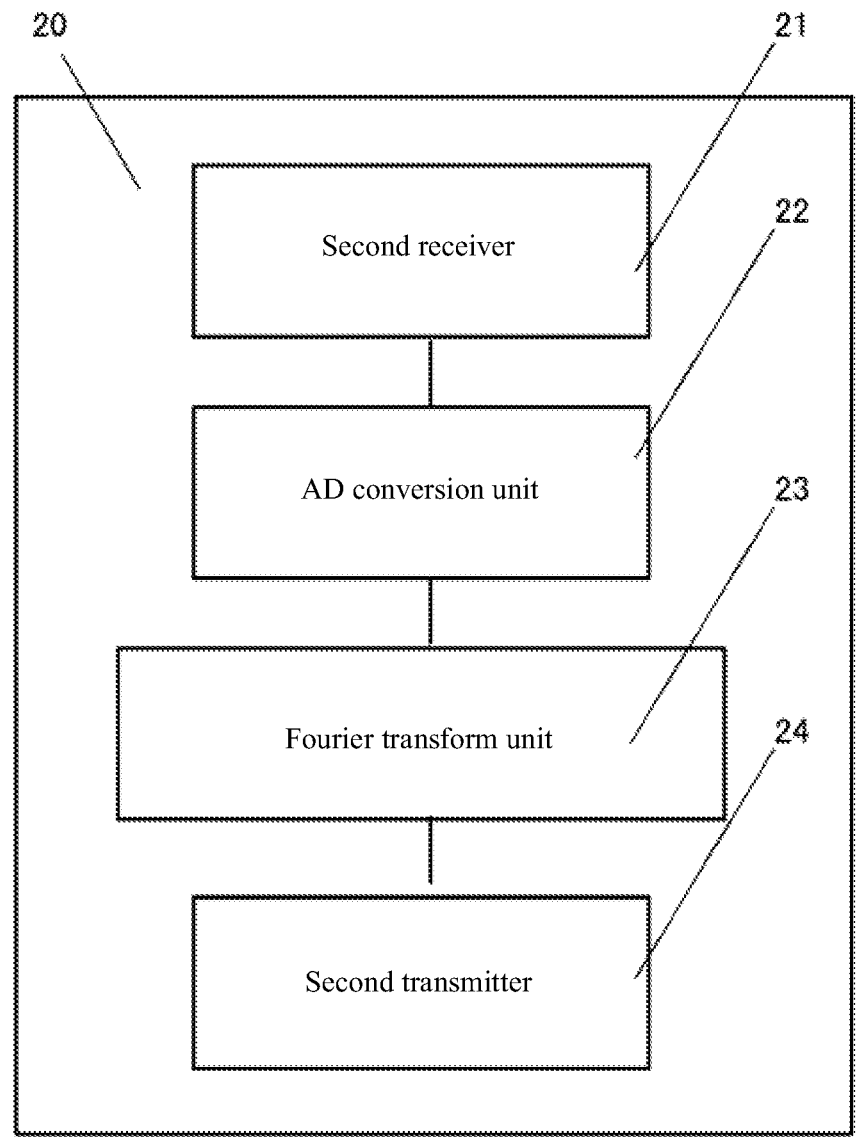
FIG. 16 is a block diagram of a controller according to an embodiment of the invention.
Figure 17:
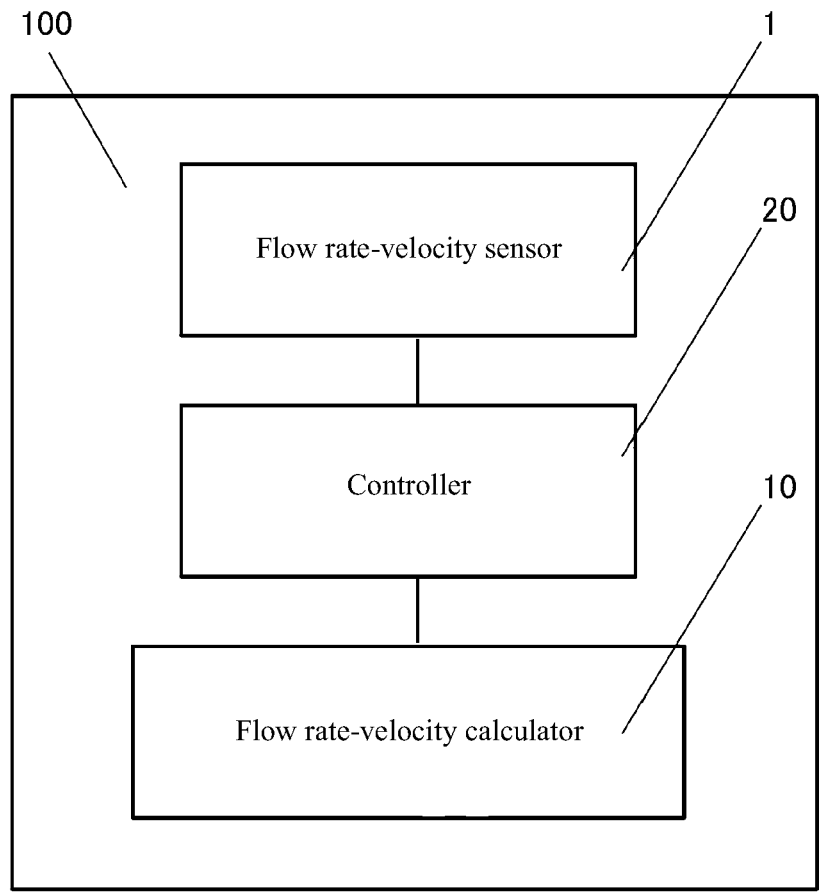
FIG. 17 is a block diagram of a flow rate-velocity sensor device according to an embodiment of the invention.
Figure 18:
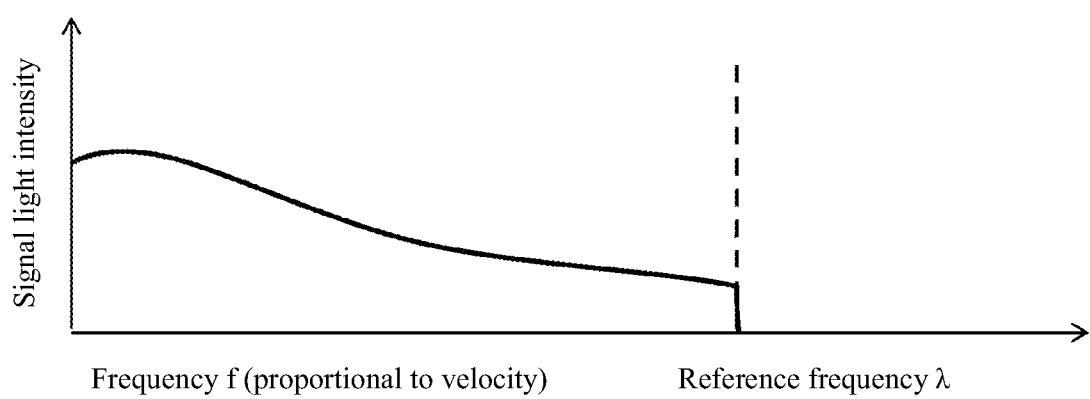
FIG. 18 is a graph yet-to-be corrected by a flow rate-velocity calculator according to an embodiment of the invention.
Figure 19:
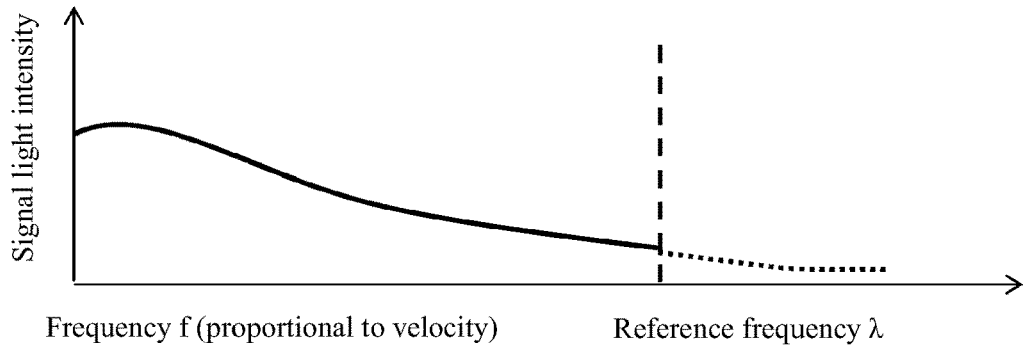
FIG. 19 is a graph corrected by a flow rate-velocity calculator according to an embodiment of the invention.
Figure 20:
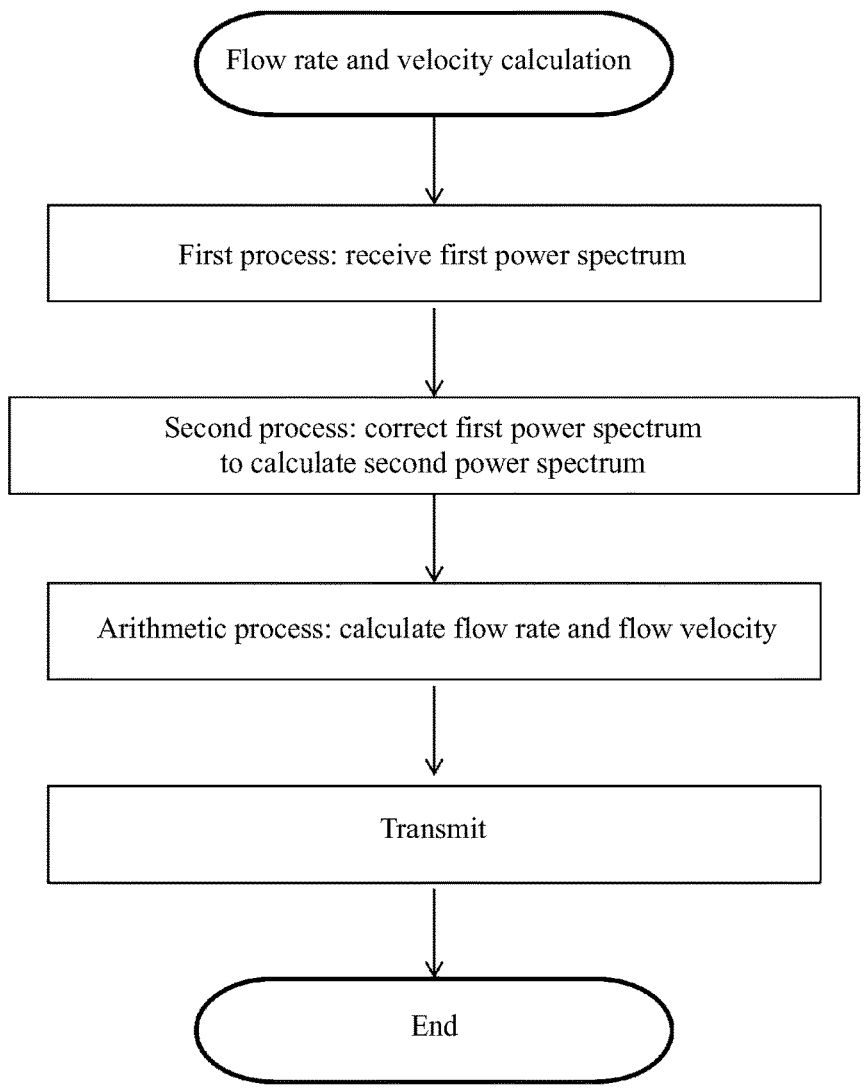
FIG. 20 is a flowchart of a flow rate-velocity calculation method according to an embodiment of the invention.
Figure 21:
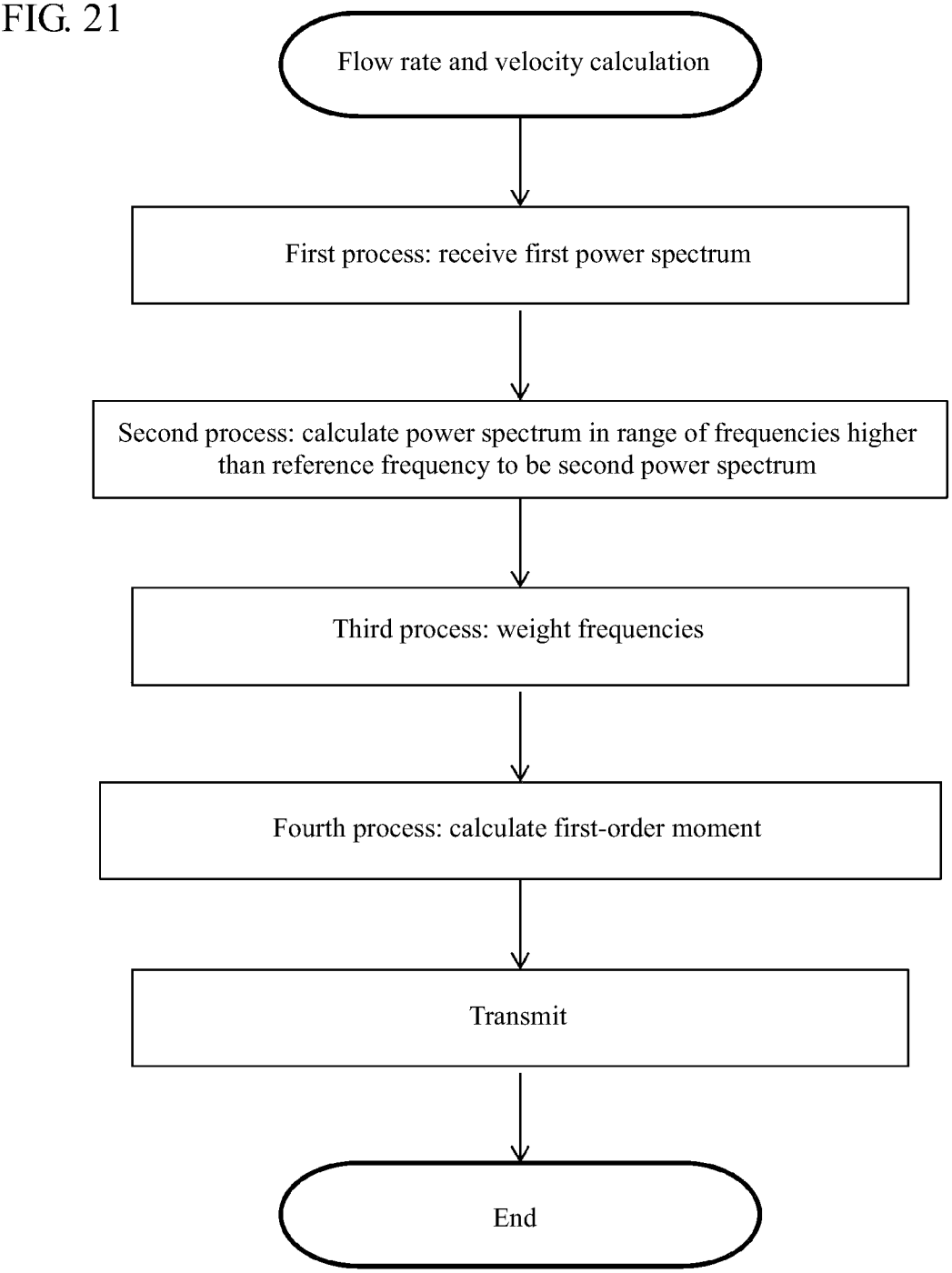
FIG. 21 is a flowchart of a flow rate-velocity calculation method according to an embodiment of the invention.
Figure 22:
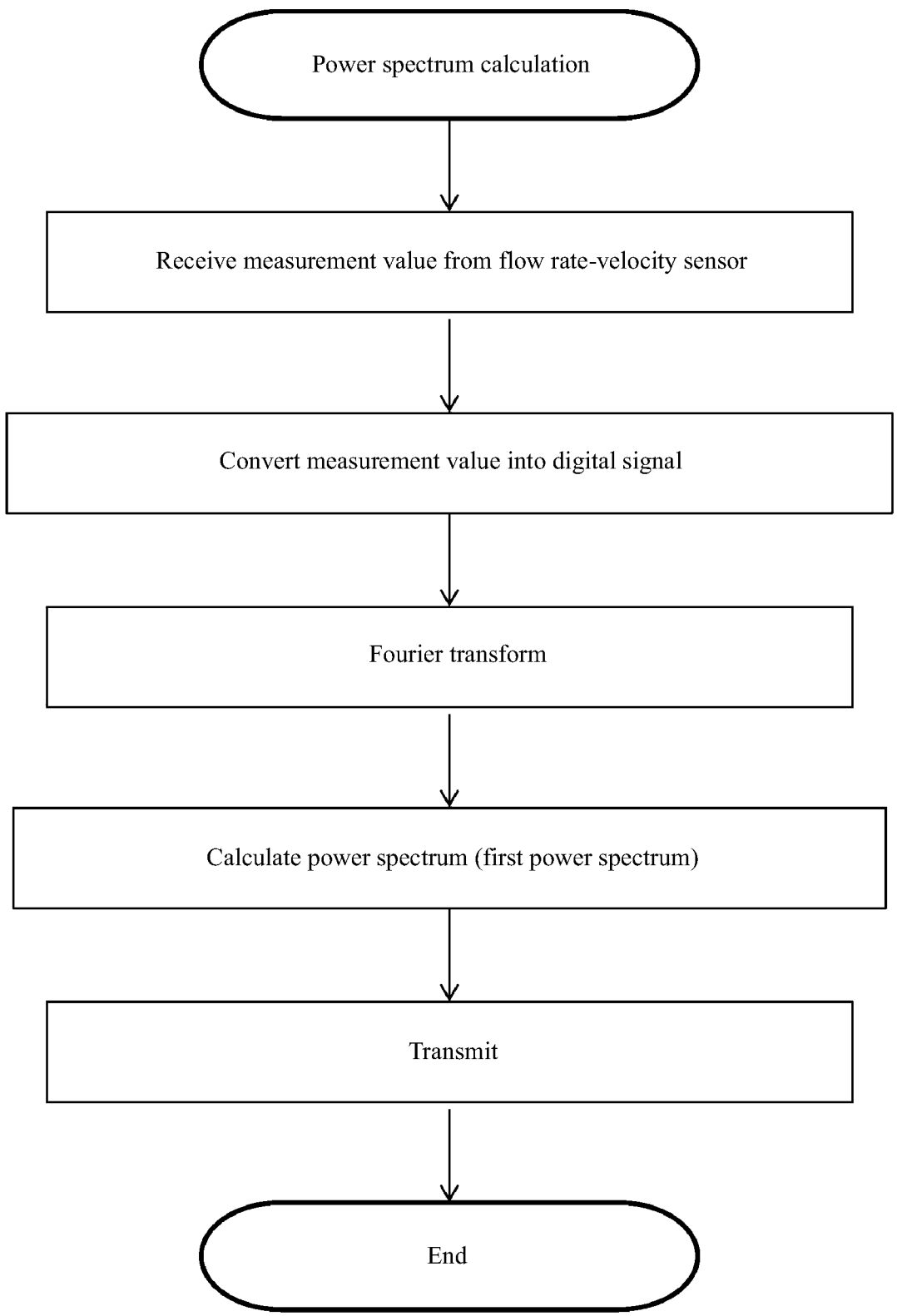
FIG. 22 is a flowchart of a flow rate-velocity calculation method according to another embodiment of the invention.
Figure 23:
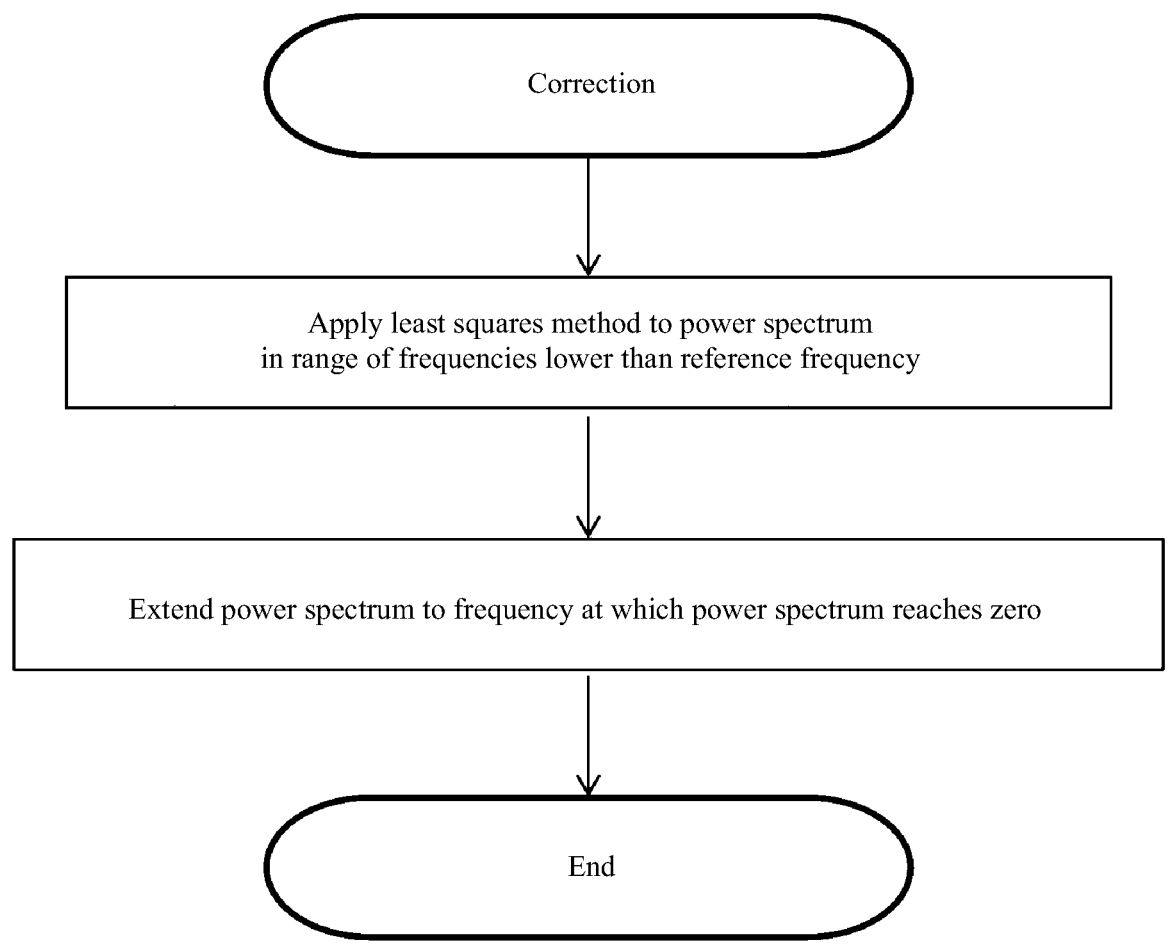
FIG. 23 is a flowchart of a flow rate-velocity calculation method according to another embodiment of the invention.
Figure 24:
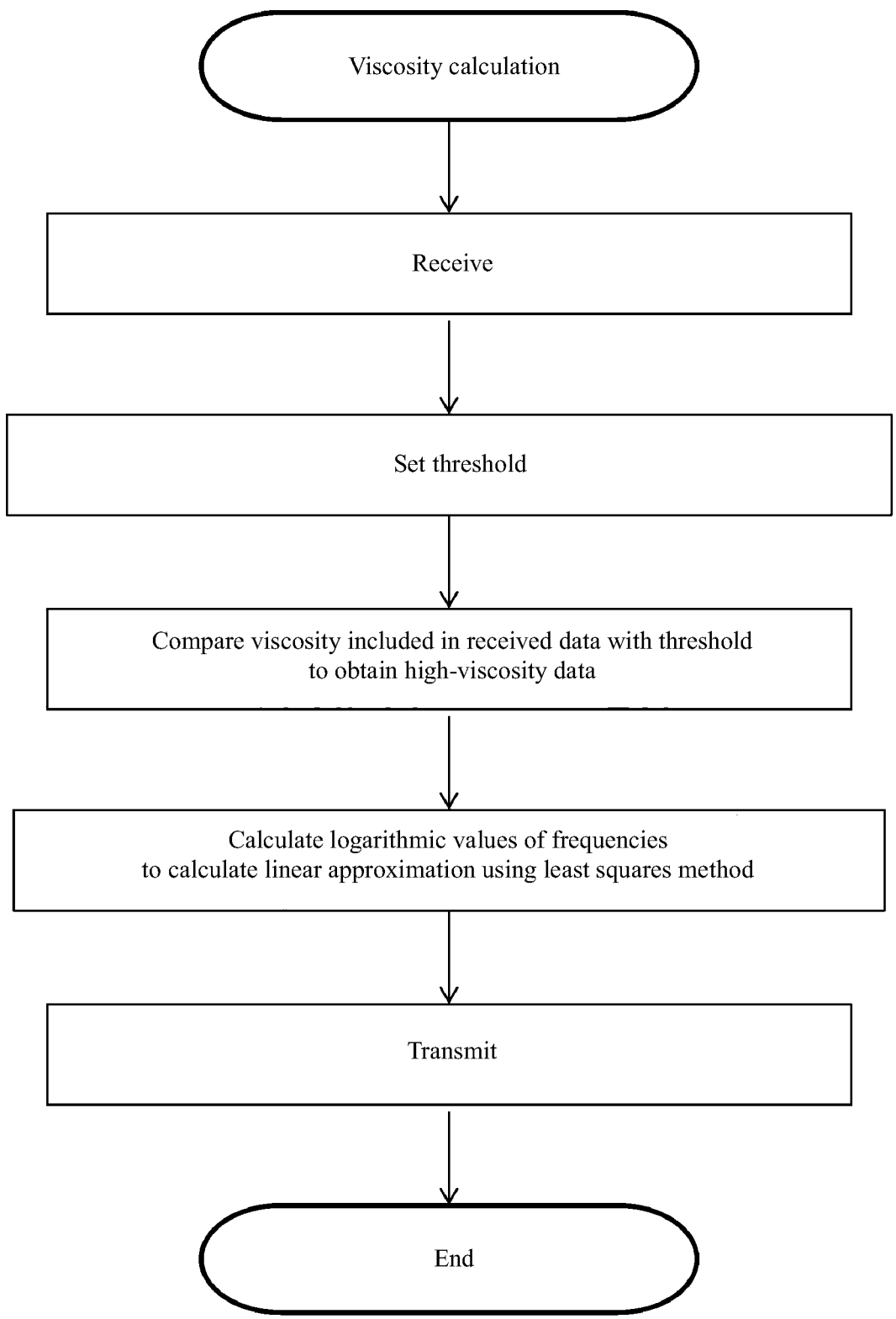
FIG. 24 is a flowchart of a flow rate-velocity calculation method according to another embodiment of the invention.
Figure 25:
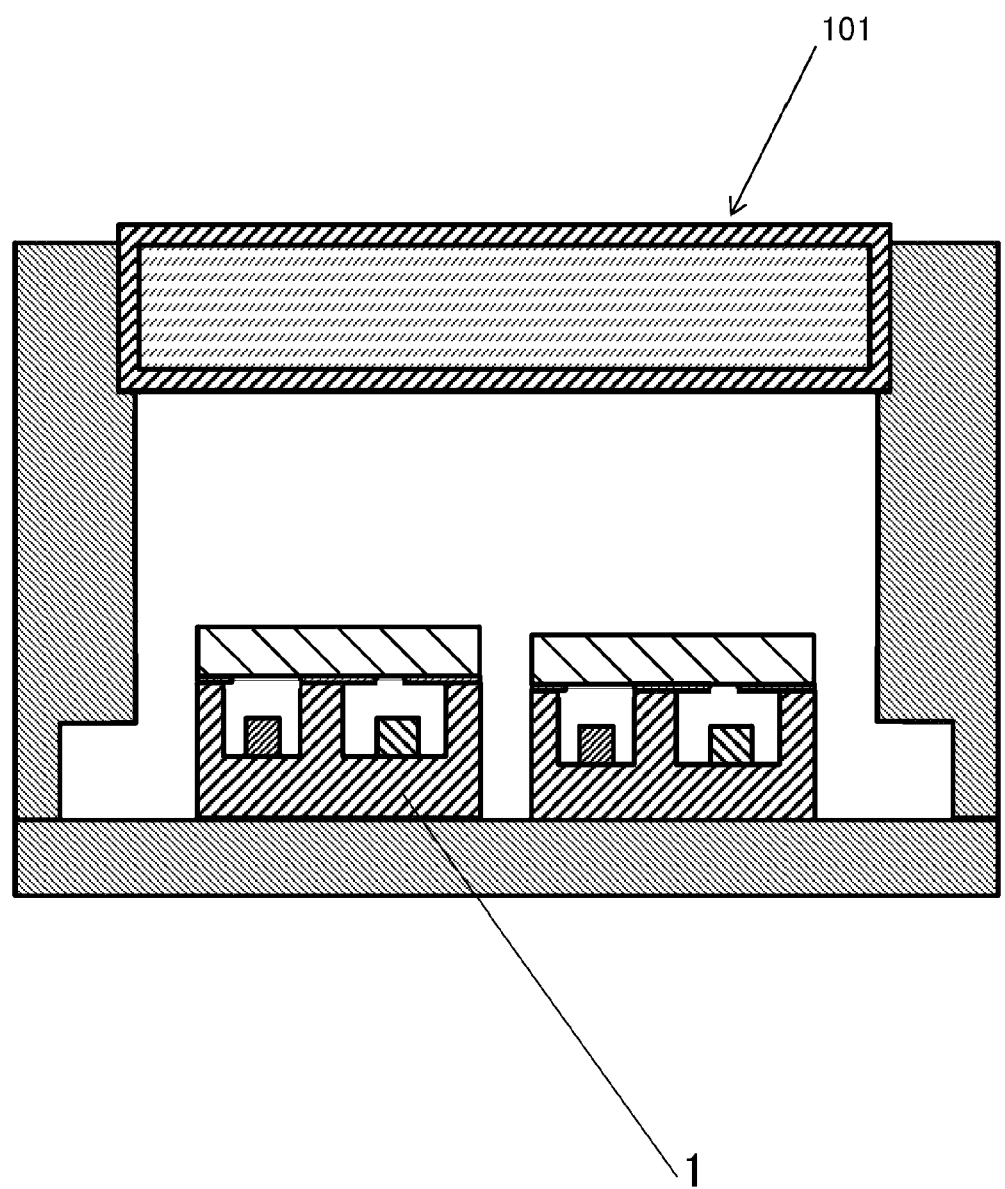
FIG. 25 is a cross-sectional view of a flow rate device according to an embodiment of the invention.

FIG. 1 is a perspective view of a flow rate-velocity sensor included in a flow rate-velocity sensor device according to an embodiment of the invention. FIG. 2 is an exploded perspective view of the flow rate-velocity sensor included in the flow rate-velocity sensor device according to the embodiment of the invention. FIG. 3 is a cross-sectional view of the flow rate-velocity sensor included in the flow rate-velocity sensor device according to the embodiment of the invention, taken along line A-A of FIG. 1. FIG. 4 is a cross-sectional view of a flow rate-velocity sensor included in a flow rate-velocity sensor device according to another embodiment of the invention. FIG. 5 is a cross-sectional view of a flow rate-velocity sensor included in a flow rate-velocity sensor device according to another embodiment of the invention. FIG. 6 is a cross-sectional view of a flow rate-velocity sensor included in a flow rate-velocity sensor device according to another embodiment of the invention. FIG. 7 is a cross-sectional view of a flow rate-velocity sensor included in a flow rate-velocity sensor device according to another embodiment of the invention. FIG. 8 is a cross-sectional view of a flow rate-velocity sensor device according to an embodiment of the invention. FIG. 9 is a cross-sectional view of a flow rate-velocity sensor device according to another embodiment of the invention. FIG. 10 is a cross-sectional view of a flow rate-velocity sensor device according to another embodiment of the invention. FIG. 11 is a cross-sectional view of a flow rate-velocity sensor device according to another embodiment of the invention. FIG. 12 is a cross-sectional view of a flow rate-velocity sensor device according to an embodiment of the invention. FIGS. 13 and 14 are block diagrams of flow rate-velocity calculators according to embodiments of the invention. FIG. 15 is a block diagram of a flow rate-velocity calculator according to another embodiment of the invention. FIG. 16 is a block diagram of a controller according to an embodiment of the invention. FIG. 17 is a block diagram of a flow rate-velocity sensor device according to an embodiment of the invention. FIG. 18 is a graph yet-to-be corrected by a flow rate-velocity calculator according to an embodiment of the invention. FIG. 19 is a graph corrected by a flow rate-velocity calculator according to an embodiment of the invention. FIGS. 20 and 21 are flowcharts illustrating the processing performed by flow rate-velocity calculation sensor devices according to embodiments of the invention. FIG. 22 is a flowchart illustrating the processing performed by a flow rate-velocity sensor device according to another embodiment of the invention. FIG. 23 is a flowchart illustrating the processing performed by a flow rate-velocity sensor device according to another embodiment of the invention. FIG. 24 is a flowchart illustrating the processing performed by a flow rate-velocity sensor device according to another embodiment of the invention. FIG. 25 is a cross-sectional view of a flow rate device according to an embodiment of the invention. In these figures, a flow rate-velocity sensor device 100 includes a flow rate-velocity sensor 1, a controller 20, and a flow rate-velocity calculator 10. The flow rate-velocity sensor 1 includes a package 2 and a transparent substrate 3. The transparent substrate 3 includes a light shield 4. The package 2 accommodates a light emitter 5 and a light receiver 6. A flow rate device 101 includes the flow rate-velocity sensor 1, a mounting board 30, a housing 50, and a flow passage 51.

The flow rate-velocity sensor device 100 according to an embodiment of the invention includes the flow rate-velocity sensor 1 for detecting the flow rate, the controller 20 for processing the detected information, and the flow rate-velocity calculator 10 for calculating the flow rate from the processed information. The flow rate-velocity sensor 1 includes a package 2 and a transparent substrate 3. The transparent substrate 3 includes a light shield 4. The package 2 accommodates a light emitter 5 and a light receiver 6. The controller 20 includes a second receiver 21, an analog-digital (AD) conversion unit 22, a Fourier transform unit 23, and a second transmitter 24. The flow rate-velocity calculator 10 includes a receiver 11, a correction unit 12, an arithmetic unit 19, and a transmitter 15. The flow rate-velocity calculation method includes a first process to a calculation process as described below.

The package 2 may be a rectangular plate as viewed from above, and may include multiple dielectric layers stacked on one another. The package 2 has, for example, a dimension of 0.5 to 5 mm as viewed from above, and a thickness of 0.5 to 5 mm. The package 2 may be, for example, a wiring board including ceramic dielectric layers, or an organic wiring board including dielectric layers of insulating resin.

The package 2 including a wiring board of a ceramic material (ceramic wiring board) includes multiple ceramic dielectric layers with conductors, such as connection pads, internal interconnections, and signal interconnections.

Examples of the ceramic material used for the ceramic wiring board include sintered aluminum oxide, sintered mullite, sintered silicon carbide, sintered aluminum nitride, sintered silicon nitride, and sintered glass ceramic.

The package 2 including a wiring board of an organic material (organic wiring board) includes multiple organic insulating layers or dielectric layers with interconnection conductors, such as signal interconnections (described later). The organic wiring board may be any wiring board including dielectric layers formed from an organic material, such as a printed wiring board, a build-up wiring board, or a flexible wiring board. Examples of the organic material used for the organic wiring board include an epoxy resin, a polyimide resin, a polyester resin, an acrylic resin, a phenol resin, and a fluorine-based resin. Such an organic material may contain filler particles or glass cloth.

The package 2 has at least two recesses, which may be referred to herein as openings, or specifically, a first opening 2a for accommodating the light receiver 6 and a second opening 2b for accommodating the light emitter 5. The first opening 2a and the second opening 2b are open in the same main surface (first surface) of the package 2.

The package 2 may include a substrate 2f and a frame 2g bonded together. The substrate 2f may include an organic material, and the frame 2g may include a ceramic material to reduce noise in the frame 2g and allow easy manufacture of the package 2.

The flow rate-velocity sensor 1 in an embodiment of the invention may be used as a measurement sensor to measure fluid flow, such as blood flow, using the Doppler effect of light. To use the Doppler effect of light, the measurement sensor includes a light emitter, which illuminates an object to be measured with light, and a light receiver, which receives light scattered by the object. When measuring, for example, blood flow, the measurement sensor illuminates a body part, such as a finger, with external light, and receives light scattered at blood cells in the blood flowing through blood vessels under the skin to measure the blood flow based on changes in the frequency. In the flow rate-velocity sensor 1, the light emitter 5 and the light receiver 6 are at a predetermined distance from each other based on the positional relationship between the illumination light and the scattered light. The first opening 2a and the second opening 2b are positioned in accordance with the positional relationship between the light receiver 6 and the light emitter 5.

The first opening 2a and the second opening 2b may be sized in accordance with the size of the light receiver 6 and the size of the light emitter 5 to be accommodated in the recesses. When, for example, a vertical-cavity surface-emitting laser (VCSEL) element is used as the light emitter 5, the first opening 2a may have a rectangular opening or a square opening, which has, for example, a longitudinal dimension of 0.3 to 2.0 mm, a lateral dimension of 0.3 to 2.0 mm, and a depth of 0.3 to 1.0 mm. In some embodiments, a light-emitting diode (LED) may be used instead.

When a surface incident photodiode is used as the light receiver 6, the second opening 2b may have a rectangular opening or a square opening, which has, for example, a longitudinal dimension of 0.3 to 2.0 mm, a lateral dimension of 0.3 to 2.0 mm, and a depth of 0.4 to 1.5 mm. The first opening 2a and the second opening 2b (the light receiver 6 and the light emitter 5) may be at any distance long enough to prevent light from the light emitter from directly entering the light receiver 6. A light-shield wall may be placed between the first opening 2a and the second opening 2b (between the light receiver 6 and the light emitter 5) to allow for a shorter distance between the first opening 2a and the second opening 2b (between the light receiver 6 and the light emitter 5).

The first opening 2a and the second opening 2b may be circular or in any other shape. The first opening 2a and the second opening 2b may each have a uniform cross section across the main surface of the package 2 in the depth direction. The first opening 2a and the second opening 2b may be recesses each having a step, or in other words, each having the same cross section as the opening to a predetermined depth, and then having a smaller, uniform cross section from the predetermined depth to the bottom. A recess with a step serving as the first opening 2a has a mount for the light receiver 6 at the bottom. A recess with a step serving as the second opening 2b has a mount for the light emitter 5 at the bottom. Each recess receives a connection pad on the step for electrical connection to the light emitter 5 or the light receiver 6.

The package 2 may include signal interconnections electrically connected to the light emitter 5 or the light receiver 6 to transmit electric signals input into the light emitter 5 or output from the light receiver 6. Each signal interconnection may include a bonding wire, which is a connector connected to the light emitter 5 or the light receiver 6, a connection pad, to which the bonding wire is connected, a via conductor, which is electrically connected to the connection pad and extends from immediately below the connection pad to the lower surface (second surface) of the package 2, and an external connection terminal, which is electrically connected to the via conductor. Each external connection terminal is located on the lower surface of the package 2 and electrically connected, with a terminal bond such as solder, to a connection terminal on the mounting board 30, on which a measurement sensor including the flow rate-velocity sensor 1 is mountable.

To improve the wettability of the bond material such as solder and improve the corrosion resistance, the external connection terminal may include a nickel layer having a thickness of 0.5 to 10 μm and a gold layer having a thickness to 0.5 to 5 μm, which may be deposited in sequence by plating.

The transparent substrate 3 is bonded to the upper surface (first surface) of the package 2 with a bond material to cover the first surface. The transparent substrate 3 seals the first opening 2a and the second opening 2b accommodating the light receiver 6 and the light emitter 5. The transparent substrate 3 is a plate of an insulating material. The transparent substrate 3 transmits light emitted from the light emitter 5 accommodated in the second opening 2b, and light to be received by the light receiver 6 accommodated in the first opening 2a.

The light emitter 5 may be a semiconductor laser element such as a vertical-cavity surface-emitting laser (VCSEL). The light receiver 6 may be a photodiode such as a silicon photodiode, a GaAs photodiode, an InGaAs photodiode, or a germanium photodiode. The light emitter 5 and the light receiver 6 may be selected as appropriate in accordance with the type of an object to be measured or the parameters to be measured.

For example, the VCSEL that can emit a laser beam with a wavelength of 850 nm may be used as the light emitter 5 for measuring blood flow using the Doppler effect of light. To measure another object, another device that emits a laser beam with a wavelength appropriate for the measurement object may be selected as the light emitter 5. With a laser beam emitted from the light emitter 5 and having its wavelength unchanged, any light receiver that can receive such a beam may be used as the light receiver 6. With a laser beam emitted from the light emitter 5 and having its wavelength changed, any light receiver that can receive such a beam with its wavelength changed may be used as the light receiver 6. Emitted light refers to light emitted directly from the light emitter 5. Illumination light (described later) refers to light illuminating a measurement object after being emitted from the light emitter 5. Scattered light refers to light scattered while, for example, passing through the transparent substrate 3 after emitted from the light emitter 5 and reflected on the inner wall.

Although the light emitter 5 and the light receiver 6 are electrically connected to the connection pad with, for example, bonding wires 32 in the present embodiment, the connection may be achieved with another method, such as flip chip connection, a method using bumps, or a method using an anisotropic conductive film.

The transparent substrate 3 transmits the illumination light and the scattered light to and from a measurement object. The characteristics of the illumination light and the scattered light depend on the light emitter used. The transparent substrate 3 may thus at least transmit the light emitted from the light emitter used. The transparent substrate 3 may be formed from an insulating material having a light transmissivity of at least 70%, or specifically at least 90% for the wavelength of light emitted from the light emitter.

Examples of the insulating material for the transparent substrate 3 include a transparent ceramic material such as sapphire, a glass material, and a resin material. Examples of the glass material include borosilicate glass, crystallized glass, quartz, and soda glass. Examples of the resin material include a polycarbonate resin, an unsaturated polyester resin, and an epoxy resin. The transparent substrate 3 is, for example, rectangular as viewed from above and has dimensions of 0.5×1 mm to 5×5 mm, with a thickness of 0.5 to 5 mm.

The bond material bonds the package 2 to the transparent substrate 3. More specifically, the bond material bonds the upper surface of the package 2 to the lower surface of the transparent substrate 3 at their outer peripheries. The bond material is continuously applied along the upper surface of the package 2, and serves as a sealant that provides airtightness and water tightness inside the first opening 2a and the second opening 2b in the package 2. The light receiver 6 and the light emitter 5 to be accommodated in the first opening 2a and the second opening 2b are susceptible to moisture. To prevent entry of external moisture, the bond material is continuously applied.

The bond material may be light-shielding. This light-shielding bond material reduces entry of external light in the first opening 2a or the second opening 2b through the gap between the package 2 and the transparent substrate 3.

The bond material may absorb light for light-shielding. The bond material may reflect light for light-shielding to prevent entry of external light. However, the bond material in this case may reflect any stray light inside the measurement sensor, which may then be received by the light receiver. The bond material that absorbs light reduces entry of external light and also absorbs internal stray light.

The bond material may include a material that absorbs light for light-shielding. The bond material may be a resin adhesive, such as an epoxy resin or a conductive silicone resin, which bonds the package 2 and the transparent substrate 3 together, with a light-absorbing material dispersed in the resin adhesive. Examples of the light-absorbing material include inorganic pigments. Examples of the inorganic pigments include carbon pigments such as carbon black, nitride pigments such as titanium black, and metal oxide pigments such as Cr—Fe—Co, Cu—Co—Mn, Fe—Co—Mn, and Fe—Co—Ni—Cr pigments. The conductive bond material may be formed from a metal material such as solder. Examples of such conductive bond materials include a brazing material, such as Sn—Ag, Sn—Ag—Cu, Au—Sn, Au—Sn—Ag, or Au—Si.

The transparent substrate 3 includes the light shield 4 on its lower surface. The light shield 4 may be formed by, for example, vapor deposition, sputtering, or baking of a metal material such as Cr, Ti, Al, Cu, Co, Ag, Au, Pd, Pt, Ru, Sn, Ta, Fe, In, Ni, and W or an alloy of these metals. The light shield 4 has a thickness of, for example, 50 to 400 nm.

The light shield 4 has a first through-hole 2c and a second through-hole 2d. The first through-hole 2c aligns with the first opening 2a as viewed from above. The second through-hole 2d aligns with the second opening 2b as viewed from above. The second through-hole 2d aligns with the light emitter 5. The first through-hole 2c is, for example, circular or rectangular, and has a dimension of 50 μm to 1 mm across. The second through-hole 2d is, for example, circular or rectangular, and has a dimension of 5 to 500 μm across. As described above, the light shield 4 covers an area of the transparent substrate 3 except an area through which light from the light emitter 5 is to be transmitted. This reduces light leaking through the covered area of the transparent substrate 3, and thus reduces light entering the light receiver 6 after leaking and being reflected on a measurement object in an unintended manner.

The flow rate-velocity calculator 10 includes the receiver 11, the correction unit 12, the arithmetic unit 19, and the transmitter 15. The receiver 11 receives data (e.g., electric signals) from an external unit. The transmitter 15 transmits data (e.g., electric signals) to the external unit. The received data includes a power spectrum P(fn), where fn represents frequency. The power spectrum P(fn) corresponds to a first power spectrum. The power spectrum P(fn) has power spectrum components with frequencies lower than a reference frequency λ. In this power spectrum, the reference frequency λ (described later) depends on the sampling rate of an analog-digital converter that converts analog values measured by the flow rate-velocity sensor 1 into digital data (AD conversion). This sampling rate excludes data with frequencies higher than the reference frequency λ. For example, power spectrum data may be divided by frequency, and used to create a graph of power versus flow rate for each frequency. The frequencies (range of frequencies) used for calculation may be determined in accordance with the flow rates (range of flow rates) to be measured.

The correction unit 12 performs correction based on data received by the receiver 11 to calculate a power spectrum (second power spectrum) for calculating at least one of the flow rate or flow velocity. For example, the correction unit 12 may include an extrapolator 18 for extrapolating data, or may select and determine the frequency to be used for calculation in accordance with the range of flow rates to be measured as described above. The correction unit 12 including the extrapolator 18 calculates and extrapolates, as the second power spectrum, a power spectrum in a range of frequencies higher than the reference frequency λ based on data received by the receiver 11. More specifically, the correction unit 12 calculates an approximation curve for the range of frequencies higher than the reference frequency λ in the first power spectrum received by the receiver 11 by applying the least squares method to the values of the power spectrum in the range of frequencies lower than the reference frequency λ in the first power spectrum. This approximation curve is used to extrapolate the power spectrum received by the receiver 11 to a frequency at which the power spectrum extended toward higher frequencies reaches zero. The power spectrum may be extrapolated to a frequency at which the power spectrum reaches below a baseline. The baseline represents an output dependent on the noise level in the spectrum. The second power spectrum asymptotically converges to a certain value. The asymptote may be used as the baseline. The correction unit 12 incorporates a program enabling such calculation. FIG. 18 shows a graph before extrapolation. In the graph, the horizontal axis indicates frequency, and the vertical axis indicates the power spectrum (signal light intensity). FIG. 19 shows a graph after extrapolation including an extrapolated dotted line.

The correction unit 12 may further include a setting unit 16 for setting a threshold B for the viscosity of an object to be measured (measurement object), and a selector 17 for performing a first approximation on viscosities lower than the threshold B set by the setting unit 16, and performing a second approximation on viscosities higher than the threshold B set by the setting unit 16. Each of the first and second approximations may be any approximation as appropriate, such as a quadratic approximation or a logarithmic approximation. The pattern of the approximation may be stored in the selector 17, together with a program for calculating the pattern.

The correction unit 12 may correct the flow rate in accordance with the amount of light received by the light receiver 6. The measurement value of the flow rate depends on the fluid concentration. The change in concentration is detected by measuring the amount of received light and is used to correct the flow rate. More specifically, the correction unit 12 may define a reference value for the concentration expressed using a direct current (DC) value, and determine the change rate of the DC value and cumulatively reflect the change rate in the flow rate value to calculate the flow rate.

The amount of reflected light or other light is affected by, for example, blood vessels and tubes through which a fluid is flowing. The amount of transmitted light or reflected light with no fluid may be estimated using an additional light-receiving sensor or using a light-receiving sensor included in the flow rate-velocity sensor device 100. In this case, the correction unit 12 may further incorporate a program for calculating the refractivity of blood vessels or tubes using the amount of reflected light, and a program for estimating the absorptivity using refractivity and transmissivity calculated from the amount of transmitted light received by the light-receiving sensor. The estimated refractivity and absorptivity can be used to estimate the signal level of received light reflecting from the inside of the measurement tube. The correction unit 12 may obtain the value multiplied by the amount of received light expressed using a DC value, and subtract the amount of reflected light from the resultant value to calculate the flow rate. The correction unit 12 may further include an additional receiver for receiving transmissivity information from the light-receiving sensor. The light-receiving sensor may include an additional transmitter for transmitting information to the flow rate-velocity calculator 10. In some embodiments, the correction unit 12 may adjust the intensity of emission from the VCSEL in accordance with the amount of received light expressed using a DC value.

The light-receiving sensor may be integral with the flow rate-velocity sensor device 100, which will be described later. These two components may be connected to each other with, for example, a flexibly movable rubber or a spring, to allow an object to be placed between them for measurement.

The arithmetic unit 19 calculates at least one of the flow rate or flow velocity from the power spectrum corrected by the correction unit 12. The arithmetic unit 19 may include, for example, a first arithmetic unit 13 and a second arithmetic unit 14. The first arithmetic unit 13 weights frequencies of the power spectrum calculated by the correction unit 12. More specifically, the first arithmetic unit 13 may use Formula 1.

$$f_n \cdot P(f_n) \qquad \text{Formula 1}$$

The first arithmetic unit 13 thus calculates a power spectrum (third power spectrum) with the weighted frequencies.

The second arithmetic unit 14 integrates the power spectrum weighted by the first arithmetic unit 13 using Formula 2.

$$\Sigma f_n \cdot P(f_n) \qquad \text{Formula 2}$$

The integration converts the power spectrum into a first-order moment.

The flow rate-velocity calculator 10 may be incorporated in the package 2 for downsizing. In some embodiments, the flow rate-velocity calculator 10 may be mounted on the mounting board 30 (described later). This structure reduces noise in the flow rate-velocity sensor 1.

The controller 20 receives the data obtained by the flow rate-velocity sensor 1 (measurement value) in the form of, for example, an electric signal. The controller 20 includes the second receiver 21 for receiving the data measured by the flow rate-velocity sensor 1, and the second transmitter 24 for transmitting data to the flow rate-velocity calculator 10.

The controller 20 includes the AD conversion unit 22 for converting measurement signals (analog signals) received by the second receiver 21 into digital signals. The controller 20 also includes the Fourier transform unit 23 for performing a Fourier transform of the data obtained by the AD conversion unit 22. The data resulting from the Fourier transform is then transmitted to the second transmitter 24 in the form of, for example, an electric signal.

The flow rate-velocity sensor device 100 may further include a display 40 for receiving and visually presenting the data obtained by the flow rate-velocity calculator 10. The display 40 allows any user to recognize the current flow rate.

The flow rate-velocity sensor device 100 according to the embodiment of the invention with the above structure more accurately calculates at least one of the flow rate or flow velocity by correcting the received power spectrum. Correcting data with the range of frequencies higher than the reference frequency λ enables more accurate calculation reflecting the difference between high flow rates and low flow rates. The flow rate-velocity sensor device 100 can thus calculate measurement values for different flow rates.

Method of Manufacturing Flow Rate-Velocity Sensor

A method of manufacturing the flow rate-velocity sensor 1 will now be described. The package 2 is produced by, for example, stacking ceramic green sheets or building up layers, in the same manner as for a multi-layer wiring board. For the package 2 that is a ceramic wiring board using alumina as a ceramic material, the powders of raw materials such as alumina ($Al_2O_3$), silica ($SiO_2$), calcium oxide (CaO), and magnesia (MgO) are mixed with an appropriate organic solvent to form slurry. The slurry is then shaped into a sheet using a known method such as a doctor blade or by calendering to produce a ceramic green sheet (hereafter also referred to as a green sheet). The green sheet is then punched into a predetermined shape. The powders of raw materials such as tungsten (W) and a glass material are mixed with an organic solvent to form a metal paste. The metal paste is then applied in a predetermined pattern by, for example, screen printing on the surface of the green sheet. The green sheet has through-holes formed and filled with the metal paste by, for example, screen printing to form via conductors. The metallized layer to be a ground conductor layer is formed on an outermost surface with the metal paste. Multiple green sheets prepared in this manner are stacked on one another, and then fired together at about 1600° C. to complete the package 2. The substrate 2f of the package 2 containing an organic material may be molded using a mold having a predetermined shape by transfer molding or injection molding. The package 2 may be formed from a glass epoxy resin, which is a base glass fiber impregnated with a resin. The base glass fiber is impregnated with a precursor of an epoxy resin. The epoxy resin precursor is then cured by heat at a predetermined temperature to form the package 2.

The transparent substrate 3 is prepared by shaving or cutting a glass material into a predetermined shape. The light shield 4 (described later) is formed on the lower surface of the transparent substrate 3 by, for example, vapor deposition, sputtering, or baking.

In the above structure, the via conductors vertically extend linearly in the package 2. The via conductors may not extend linearly, and may be displaced inside the package 2 due to, for example, an inner layer interconnection or an internal ground conductor layer when the package 2 has the upper surface electrically connected to external connection terminals on the lower surface.

Other Embodiments of Flow Rate-Velocity Sensor

A flow rate-velocity sensor device 100 according to another embodiment of the invention may include a lens 8 attached to an upper surface of a transparent substrate 3. The lens 8 is aligned with a first opening 2a and a first through-hole 2c. The lens 8 has a diameter of, for example, 20 μm to 2 mm as viewed from above, and a thickness of 0.5 to 2 mm. The lens 8 may be formed from, for example, a glass material such as quartz glass or borosilicate glass, or a resin material such as acrylic, polycarbonate, styrene, or polyolefin. The lens 8 may be transmissive to allow light from a light emitter 5 to travel to a light receiver 6. The lens 8 may be a collecting lens, such as a convex lens, that refracts light in the optical axis direction. The lens 8 refracts diffusive light from the light emitter 5 into convergent or collimated light, and thus can more effectively collect light to be delivered to the light receiver 6.

The flow rate-velocity sensor device 100 may further include a second lens 9 attached to the upper surface of the transparent substrate 3. The second lens 9 is aligned with a second opening 2b and a second through-hole 2d. The second lens 9 has a diameter of, for example, 70 μm to 2 mm as viewed from above, and a thickness of 50 μm to 2 mm. The second lens 9 may be formed from, for example, a glass material such as quartz glass or borosilicate glass, or a resin material such as acrylic, polycarbonate, styrene, or polyolefin. The second lens 9 may be transmissive to allow light from the light emitter 5 to pass. The second lens 9 may be a collecting lens, such as a convex lens, that refracts light in the optical axis direction. The second lens 9 refracts diffusive light from the light emitter 5 into convergent or collimated light, and thus can more effectively collect light. A single lens may extend over a VCSEL and a photodiode (PD) to collect light emitted from the VCSEL and light to be received by the PD.

The flow rate-velocity sensor 1 including either the lens 8 or the second lens 9 or both calculate the flow velocity using light from a point in a fluid directed through the lenses and a light shield 4. The flow passage has the distribution of velocities lower outward and higher inward. Thus, information about the flow velocity can be obtained at any intended measurement point in the passage using the lenses. The information may then be used to calculate the flow rate reflecting the flow velocity, the cross-sectional area, and the viscosity.

Measuring the flow rate at such inward positions in the passage may be preceded by determining the depth positions at which measurement can be performed by the flow rate-velocity sensor device 100. Such measurable depths can be calculated theoretically by the formula below, indicating that the Doppler shift is larger as light reaches deeper positions. Such measurable depths may be obtained as actual measurement values using a device described below.

$$|\Delta f| \approx \frac{f_0}{c} \left| \sum_{i=1}^{N} v_i (\cos\theta_i - \cos\theta_{i+1}) \right|$$ Formula 3

An example device includes a first substrate receiving a laser diode (LD), and a second substrate receiving a PD. The distance between the first and second substrates may be variable for measurement. The flow rate-velocity sensor device 100 may be located at an end of each substrate. The flow rate-velocity sensor device 100 may estimate the depth of a measurement position by calculating a change in the amount of received light in response to a change in the distance between the first and second substrates. Each of the first and second substrates may include wireless communication sensors (reception and transmission sensors) and a distance sensor (e.g., a Time-of-Flight or TOF sensor). In some embodiments, one of the first and second substrates may include an arithmetic unit incorporating a program for calculating the results from detecting the distance and the light. The distance between the first and second substrates may be variable automatically. In this case, the device may estimate a depth in a manner flexible for a variety of measurement objects. In some embodiments, the flow rate-velocity sensor device may include a single substrate with two or more sensors mounted along the flow passage as in a flow rate device 101. The single substrate with two or more sensors can function in a similar manner to the substrates that can vary the distance between the LD and the PD. The substrate does not move and also avoids varying distances between the sensors. This structure includes two or more flow rate-velocity sensors 1 that are mounted on the mounting board 30 along the flow passage 51 attached to the housing 50.

A flow rate-velocity sensor 1 according to another embodiment of the invention may further include a second light receiver 7 accommodated in a first opening 2a. In this embodiment, a light shield 4 may have an opening over the second light receiver 7 to receive light radiated toward the second light receiver 7. This reduces ambient light reaching the second light receiver 7.

In a flow rate-velocity sensor 1 according to another embodiment of the invention, a light shield 4 may have a third through-hole 2e that aligns with a second opening 2b and is at a distance from a second through-hole 2d. The third through-hole 2e may be located between a first through-hole 2c and a second through-hole 2d. The third through-hole 2e, which receives reference light, allows light to travel to a light receiver 6 more precisely, thus enabling more accurate velocity calculation. In this embodiment, the third through-hole 2e may be smaller than the second through-hole 2d.

In a flow rate-velocity sensor 1 according to another embodiment of the invention, a clearance is left between a lower surface of a transparent substrate 3 and a package 2 between a first opening 2a and a second opening 2b. More specifically, the package 2 includes a light-shield wall between the first opening 2a and the second opening 2b. The light-shield wall has a partially recessed upper end that allows reference light to pass and directly reach a light receiver 6, thus allowing more accurate measurement.

Other Embodiments of Flow Rate-Velocity Sensor Device

A flow rate-velocity sensor 1 may be mounted on a mounting board 30 for use. A controller 20 may also be mounted on the mounting board 30. The controller 20 may include a control unit for controlling light emission of a light emitter 5, and an arithmetic element for calculating blood flow velocity and other parameters based on signals output from a light receiver 6. The flow rate-velocity sensor 1 may be housed in a housing 50. The housing 50 reduces external noise.

To start measurement, the fingertip of a finger to be a measurement object is placed into contact with the surface of a transparent substrate 3. In this state, a light emitter control current is provided from the mounting board 30 into the flow rate-velocity sensor 1 through an external connection terminal, and input into the light emitter 5 through a via conductor and a connection pad. Light for measurement is then emitted from the light emitter 5. When the emitted light is applied to the fingertip through the transparent substrate 3, the light is scattered by blood cells in the blood. When receiving the scattered light transmitted through the transparent substrate 3, the light receiver 6 outputs an electric signal corresponding to the amount of received light. The output signal then passes through the connection pad and the via conductor, and is output from the flow rate-velocity sensor 1 to the mounting board 30 through the external connection terminal.

In the mounting board 30, a signal output from the flow rate-velocity sensor 1 is input to the arithmetic unit, which can then calculate the blood flow velocity by analyzing the intensity of scattered light received by the light receiver 6 for each frequency.

Flow Rate-Velocity Calculation Method

The flow rate-velocity calculation method is the same in detail as the program incorporated in the above flow rate-velocity calculator and will not be described. With the flow rate-velocity calculation method, a measurement value resulting from analog-digital conversion is corrected and used for calculation in the manner described below. The method includes a first process of calculating a first power spectrum from data resulting from analog-digital conversion, a second process of correcting the first power spectrum obtained in the first process to calculate a second power spectrum by extrapolating a power spectrum in the range of frequencies higher than the reference frequency $\lambda$ and a calculation process of calculating at least one of the flow rate or the flow velocity from the second power spectrum corrected in the second process. The calculation process includes a third process of weighting frequencies based on the second power spectrum corrected in the second process, and a fourth process of calculating a first-order moment for the third power spectrum obtained in the third process.

The second process may use the least squares method. The second process may use a linear approximation for extrapolation to a frequency at which the power spectrum reaches zero.

The second process may include setting the threshold B for the viscosity of a measurement object included in the data from the first process. The second process may also include a first approximation on viscosities higher than the set threshold B, and a second approximation on viscosities lower than the threshold B.

The flowcharts of FIGS. 21 to 24 will now be described. FIG. 21 is a simplified flowchart showing the flow rate-velocity calculation method including transmission of data, in addition to the first to fourth processes. FIG. 22 is a flowchart showing the processing up to transmission of data detected by the flow rate-velocity sensor 1 to the flow rate-velocity calculator 10. FIG. 23 is a flowchart showing specific extrapolation included in the second process. FIG. 24 is a flowchart showing a method of calculating the fluid viscosity for calculating the flow rate reflecting the fluid viscosity.

The invention is not limited to the examples described in the above embodiments. All the embodiments according to the invention may be variously modified, including numerical values. Any method may be used for mounting the units or devices in the embodiments. The features of one or more of the embodiments according to the invention may be combined.

REFERENCE SIGNS LIST 1 flow rate-velocity sensor
2 package
3 transparent substrate
4 light shield
5 light emitter
6 light receiver
7 second light receiver
8 lens
9 second lens
10 flow rate-velocity calculator
11 receiver
12 correction unit
13 first arithmetic unit
14 second arithmetic unit
15 transmitter
16 setting unit
17 selector
18 extrapolator
19 arithmetic unit
20 controller
21 second receiver
22 analog-digital conversion unit
23 Fourier transform unit
24 second transmitter
30 mounting board
40 display
50 housing
51 flow passage
2a first opening
2b second opening
2c first through-hole
2d second through-hole
2e third through-hole
2f substrate
2g frame
100 flow rate-velocity sensor device
101 flow rate device
$\lambda$ reference frequency
B threshold

The invention claimed is:

1. A flow rate-velocity calculator, comprising:
a receiver configured to receive data on a first power spectrum;
a correction unit configured to correct the data received by the receiver to calculate a second power spectrum related to a reference frequency;
an arithmetic unit configured to calculate at least one of a flow rate or a flow velocity of a fluid from the second power spectrum; and
a transmitter configured to transmit data obtained through calculation by the arithmetic unit to an external unit, wherein
the receiver receives, as the first power spectrum, a power spectrum in a range of frequencies lower than the reference frequency, and
the correction unit includes an extrapolator configured to calculate, as the second power spectrum, a power spectrum in a range of frequencies higher than the reference frequency and extrapolate the second power spectrum based on the data received by the receiver.

2. The flow rate-velocity calculator according to claim 1, wherein
the correction unit determines a range of frequencies to be used for calculation in accordance with a range of flow rates to be measured.

3. The flow rate-velocity calculator according to claim 1, wherein
the correction unit reflects a change rate of a direct current value used as a reference value in at least one of the flow rate or the flow velocity.

4. The flow rate-velocity calculator according to claim 1, wherein
the correction unit calculates an absorptivity of light on a peripheral wall of a flow passage including the fluid.

5. The flow rate-velocity calculator according to claim 4, wherein
the absorptivity is calculated from at least one of a refractivity based on an amount of light reflected by the peripheral wall or a transmissivity based on an amount of light transmitted.

6. The flow rate-velocity calculator according to claim 1, wherein
the correction unit calculates an approximation curve for the range of frequencies higher than the reference frequency in the power spectrum received by the receiver by applying a least squares method to values of the power spectrum in the range of frequencies lower than the reference frequency in the power spectrum received by the receiver.

7. The flow rate-velocity calculator according to claim 6, wherein the correction unit extrapolates the power spectrum using the approximation curve to a frequency at which the second power spectrum reaches zero or below a baseline.

8. The flow rate-velocity calculator according to claim 1, wherein
the correction unit includes
a setting unit configured to set a threshold for a viscosity of a measurement object in the data received by the receiver, and
a selector configured to perform a first approximation on a viscosity higher than the threshold set by the setting unit and a second approximation on a viscosity lower than the threshold set by the setting unit.

9. The flow rate-velocity calculator according to claim 8, wherein
the first approximation is a logarithmic approximation, and the second approximation is a quadratic approximation.

10. The flow rate-velocity calculator according to claim 1, wherein
the arithmetic unit includes
a first arithmetic unit configured to weight frequencies of the second power spectrum, and
a second arithmetic unit configured to integrate a third power spectrum resulting from weighting performed by the first arithmetic unit.

11. A flow rate-velocity sensor device, comprising:
a flow rate-velocity sensor including
a package including a light receiver and a light emitter at a distance from each other, and
a transparent substrate on an upper surface of the package, the transparent substrate including a light shield on a lower surface of the transparent substrate;
a controller configured to receive data measured by the flow rate-velocity sensor; and
the flow rate-velocity calculator according to claim 1 configured to receive data from the controller.

12. The flow rate-velocity sensor device according to claim 11, wherein
the flow rate-velocity calculator is inside the package.

13. The flow rate-velocity sensor device according to claim 11, further comprising:
a mounting board on a lower surface of the flow rate-velocity sensor,
wherein the controller and the flow rate-velocity calculator are mounted on the mounting board.

14. A flow rate-velocity device, comprising:
a plurality of flow rate-velocity sensors each including
a package including a light receiver and a light emitter at a distance from each other, and
a transparent substrate on an upper surface of the package, the transparent substrate including a light shield on a lower surface of the transparent substrate;
a mounting board on which the plurality of flow rate-velocity sensors are mounted;
a housing at the mounting board;
a flow passage on the housing; and
the flow rate-velocity calculator according to claim 1 configured to receive data from the controller.

15. A flow rate-velocity calculation method, comprising:
a first process of receiving a first power spectrum;
a second process of correcting the first power spectrum received in the first process to calculate a second power spectrum related to a reference frequency; and
a calculation process of calculating at least one of a flow rate or a flow velocity from the second power spectrum, wherein
the first process includes receiving, as the first power spectrum, a power spectrum in a range of frequencies lower than the reference frequency, and
the second process includes calculating, as the second power spectrum, a power spectrum in a range of frequencies higher than the reference frequency based on data from the first process.

16. The flow rate-velocity calculation method according to claim 15, wherein
the second process uses a least squares method.

17. The flow rate-velocity calculation method according to claim 16, wherein
the second process extrapolates the second power spectrum using a linear approximation to a frequency at which the second power spectrum reaches zero or below a baseline.

18. The flow rate-velocity calculation method according to claim 15, wherein
the second process includes setting a threshold for a viscosity of a measurement object in data from the first process, performing a first approximation on a viscosity higher than the set threshold and a second approximation on a viscosity lower than the threshold.

* * * * *